(12) United States Patent
Lang et al.

(10) Patent No.: US 7,300,473 B2
(45) Date of Patent: Nov. 27, 2007

(54) COMPOSITION FOR DYEING KERATIN FIBERS WITH A CATIONIC DIRECT DYE AND A THICKENING POLYMER

(75) Inventors: Gérard Lang, Saint Prix (FR); Jean Cotteret, Verneuil sur Seine (FR)

(73) Assignee: L'Oreal S.A., Paris (FR)

(*) Notice: Subject to any disclaimer, the term of this patent is extended or adjusted under 35 U.S.C. 154(b) by 0 days.

(21) Appl. No.: 11/590,853

(22) Filed: Nov. 1, 2006

(65) Prior Publication Data

US 2007/0039107 A1 Feb. 22, 2007

Related U.S. Application Data

(63) Continuation of application No. 11/339,466, filed on Jan. 26, 2006, now abandoned, which is a continuation of application No. 10/869,058, filed on Jun. 17, 2004, now abandoned, which is a continuation of application No. 09/350,579, filed on Jul. 8, 1999, now abandoned.

(30) Foreign Application Priority Data

Jul. 9, 1998 (FR) .................. 98 08835

(51) Int. Cl.
A61K 7/13 (2006.01)

(52) U.S. Cl. .............. 8/405; 8/437; 8/552; 8/554; 8/570; 8/571; 8/573; 8/575; 8/638; 8/644; 8/654; 8/677

(58) Field of Classification Search .......... 8/405, 8/437, 552, 554, 570, 571, 573, 575, 638, 8/644, 654, 677
See application file for complete search history.

(56) References Cited

U.S. PATENT DOCUMENTS

| | | |
|---|---|---|
| 2,798,053 A | 7/1957 | Brown |
| 2,923,962 A | 2/1960 | Ackerman et al. |
| 3,869,454 A | 3/1975 | Lang et al. |
| 3,915,921 A | 10/1975 | Schlatzer et al. |
| 3,955,918 A | 5/1976 | Lang |
| 3,985,499 A | 10/1976 | Lang et al. |
| 4,025,301 A | 5/1977 | Lang |
| 4,151,162 A | 4/1979 | Lang et al. |
| 4,153,065 A | 5/1979 | Lang |
| 4,228,259 A | 10/1980 | Kalopissis et al. |
| 4,237,243 A | 12/1980 | Quack |
| 4,509,949 A | 4/1985 | Huang et al. |
| 4,823,985 A | 4/1989 | Grollier et al. |
| 5,474,578 A | 12/1995 | Chan et al. |
| 5,708,151 A | 1/1998 | Mockli |
| 5,879,412 A | 3/1999 | Rondeau et al. |
| 5,919,273 A | 7/1999 | Rondeau et al. |
| 5,976,195 A * | 11/1999 | de la Mettrie et al. ......... 8/411 |
| 5,989,295 A | 11/1999 | de la Mettrie et al. |
| 5,993,490 A | 11/1999 | Rondeau et al. |
| 6,001,135 A * | 12/1999 | Rondeau et al. ............... 8/407 |
| 6,010,541 A * | 1/2000 | de la Mettrie et al. ......... 8/412 |
| 6,074,439 A | 6/2000 | de la Mettrie et al. |
| 6,106,578 A | 8/2000 | Jones et al. |
| 6,120,780 A | 9/2000 | Dupuis |
| 6,187,057 B1 | 2/2001 | Maubru |
| 6,277,155 B1 | 8/2001 | de la Mettrie et al. |
| 6,344,063 B1 | 2/2002 | de la Mettrie et al. |
| 6,527,814 B1 | 3/2003 | de la Mettrie et al. |
| 6,613,102 B2 | 9/2003 | Lang et al. |
| 7,175,674 B2 | 2/2007 | de la Mettrie et al. |
| 2001/0047554 A1 | 12/2001 | de la Mettrie et al. |

FOREIGN PATENT DOCUMENTS

| | | |
|---|---|---|
| EP | 0 216479 | 4/1987 |
| EP | 0 503 853 | 9/1992 |
| EP | 0 714 954 | 5/1996 |
| EP | 0 801 942 | 10/1997 |
| EP | 0 815-328 | 1/1998 |
| EP | 0 827 738 | 3/1998 |
| EP | 0 827 739 | 3/1998 |
| EP | 0 850 636 | 7/1998 |
| EP | 0 850 637 | 7/1998 |
| EP | 0 850 638 | 7/1998 |
| FR | 2 140 205 | 1/1973 |
| FR | 2 189 006 | 1/1974 |
| FR | 2 282 860 | 3/1976 |
| FR | 2 285 851 | 4/1976 |
| FR | 2 416 723 | 9/1979 |
| FR | 2 586 913 | 3/1987 |
| FR | 2 633 940 | 1/1990 |
| FR | 2 751 533 | 1/1998 |
| FR | 2 757 387 | 6/1998 |

(Continued)

OTHER PUBLICATIONS

English Language Derwent Abstract for EP 0 801 942. (1997).

(Continued)

Primary Examiner—Eisa Elhilo
(74) Attorney, Agent, or Firm—Finnegan, Henderson, Farabow, Garrett & Dunner LLP

(57) ABSTRACT

The invention relates to a composition for dyeing fibers such as the hair, comprising at least one cationic direct dye of given formula, and which also contains at least one thickening polymer chosen from the group comprising: —nonionic amphiphilic polymers comprising at least one hydrophilic unit and at least one unit containing a fatty chain, —anionic amphiphilic polymers comprising at least one hydrophilic unit and at least one unit containing a fatty chain, —cationic amphiphilic polymers comprising at least one hydrophilic unit and at least one unit containing a fatty chain. The invention also relates to the dyeing processes and dyeing kits therefor.

45 Claims, No Drawings

FOREIGN PATENT DOCUMENTS

| | | |
|---|---|---|
| GB | 1 360 562 | 7/1974 |
| GB | 2 142 348 | 1/1985 |
| JP | H10-101538 | 4/1998 |
| JP | H10-182379 | 7/1998 |
| WO | WO 95/01772 | 1/1995 |
| WO | WO 95/15144 | 6/1995 |
| WO | WO 97/44002 | 11/1997 |
| WO | WO 97/44003 | 11/1997 |
| WO | WO 98/03150 | 1/1998 |

OTHER PUBLICATIONS

English Language Derwent Abstract for FR 2 633 940. (1990).

* cited by examiner

COMPOSITION FOR DYEING KERATIN FIBERS WITH A CATIONIC DIRECT DYE AND A THICKENING POLYMER

This is a continuation of application Ser. No. 11/339,466, filed Jan. 26, 2006 now abandoned, which is a continuation of application Ser. No. 10/869,058, filed Jun. 17, 2004, now abandoned, which is a continuation of application Ser. No. 09/350,579, filed on Jul. 8, 1999, now abandoned, and which claims priority benefit under 35 U.S.C. § 119 to French Application No. 98 08835, filed Jul. 9, 1998, all of which are incorporated herein by reference.

The invention relates to a composition for dyeing keratin fibres, in particular human keratin fibres such as the hair, comprising, in a medium which is suitable for dyeing, at least one cationic direct dye of given formula and at least one specific thickening polymer.

The invention also relates to the dyeing processes and dyeing devices using the said composition.

Two types of dyeing may be distinguished in the haircare sector.

The first is semi-permanent or temporary dyeing, or direct dyeing, which uses dyes capable of giving the hair a natural coloration, a more or less pronounced colour change which may withstand shampooing several times. These dyes are also known as direct dyes; they can be used with or without an oxidizing agent. In the presence of an oxidizing agent, the aim is to obtain lightening dyeing. Lightening dyeing is carried out by applying a mixture, prepared at the time of use, of a direct dye and an oxidizing agent to the hair, and makes it possible in particular to obtain, by lightening the melanin in the hair, an advantageous effect such as a unified colour in the case of grey hair, or to bring out the colour in the case of naturally pigmented hair.

The second is permanent dyeing or oxidation dyeing. This is carried out with so-called "oxidation" dyes comprising oxidation dye precursors and couplers. Oxidation dye precursors, commonly known as "oxidation bases", are compounds which are initially colourless or weakly coloured which develop their dyeing power on the hair in the presence of oxidizing agents added at the time of use, leading to the formation of coloured compounds and dyes. The formation of these coloured compounds and dyes results either from an oxidative condensation of the "oxidation bases" with themselves or from an oxidative condensation of the oxidation bases with coloration-modifying compounds commonly known as "couplers", which are generally present in the dye compositions used in oxidation dyeing.

It is known practice to add direct dyes to oxidation dyes in order to vary the shades obtained with the said oxidation dyes or to enrich the shades with glints.

Among the cationic direct dyes available in the sector of dyeing keratin fibres, in particular human keratin fibres, the compounds whose structure is developed in the text hereinbelow are already known; nevertheless, these dyes lead to colorations which have characteristics that are still unsatisfactory as regards the intensity, the homogeneity of the colour distributed along the fibre, in which case the coloration is said to be too selective, and as regards the staying power, in terms of the resistance to the various attacking factors to which the hair may be subjected (light, bad weather, shampooing).

After considerable research conducted in this matter, the Applicant has now discovered that it is possible to obtain novel compositions for dyeing keratin fibres which are capable of giving more intense and yet unselective colorations which show good resistance to the various attacking factors to which the hair may be subjected, by combining at least one specific thickening polymer with at least one known cationic direct dye of the prior art, which have the respective formulae defined below.

This discovery forms the basis of the present invention.

A first subject of the present invention is thus a composition for dyeing keratin fibres, and in particular human keratin fibres such as the hair, containing, in a medium which is suitable for dyeing, (i) at least one cationic direct dye whose structure corresponds to formulae (I) to (IV) defined below, characterized in that it also contains (ii) at least one specific thickening polymer.

(i) The cationic direct dye which can be used according to the present invention is a compound chosen from those of formulae (I), (II), (III), (III') and (IV) below:

a) the compounds of formula (I) below:

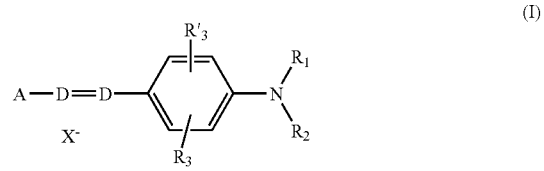

in which:

D represents a nitrogen atom or a —CH group, $R_1$ and $R_2$, which may be identical or different, represent a hydrogen atom; a $C_1$-$C_4$ alkyl radical which can be substituted with a —CN, —OH or —NH$_2$ radical or form, with a carbon atom of the benzene ring, a heterocycle optionally containing oxygen or nitrogen, which can be substituted with one or more $C_1$-$C_4$ alkyl radicals; a 4'-aminophenyl radical, $R_3$ and $R'_3$, which may be identical or different, represent a hydrogen atom, a halogen atom chosen from chlorine, bromine, iodine and fluorine, a cyano radical, or a $C_1$-$C_4$ alkyl, $C_1$-$C_4$ alkoxy or acetyloxy radical, $X^-$ represents an anion preferably chosen from chloride, methyl sulphate and acetate, A represents a group chosen from the structures A1 to A19 below:

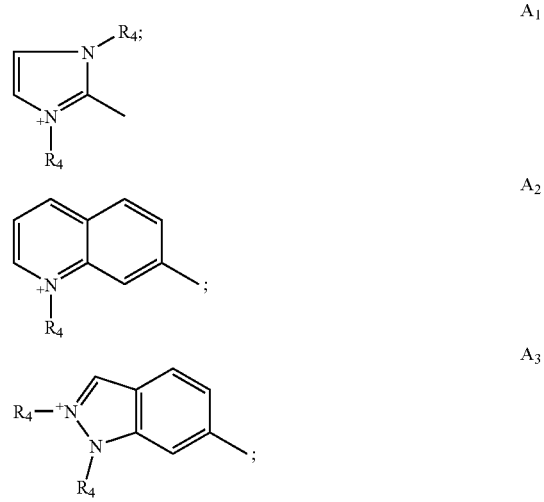

-continued

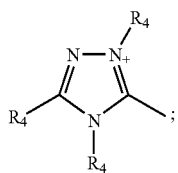

A<sub>5</sub>

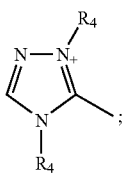

A<sub>6</sub>

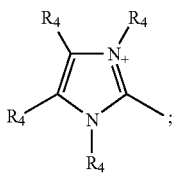

A<sub>7</sub>

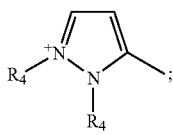

A<sub>8</sub>

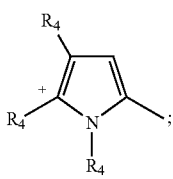

A<sub>9</sub>

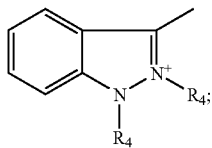

A<sub>10</sub>

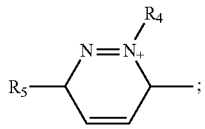

A<sub>11</sub>

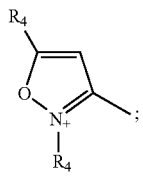

A<sub>12</sub>

-continued

A<sub>4</sub>

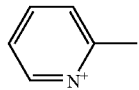

A<sub>13</sub>

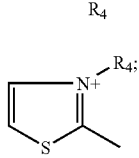

A<sub>14</sub>

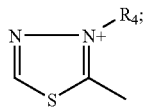

A<sub>15</sub>

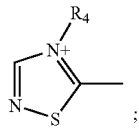

A<sub>16</sub>

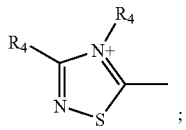

A<sub>17</sub>

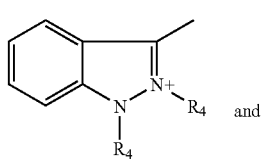 and

A<sub>18</sub>

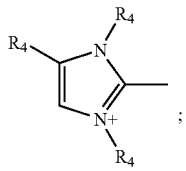

A<sub>19</sub> in which $R_4$ represents a $C_1$-$C_4$ alkyl radical which can be substituted with a hydroxyl radical and $R_5$ represents a $C_1$-$C_4$ alkoxy radical, with the proviso that when D represents —CH, when A represents $A_4$ or $A_{13}$ and when $R_3$ is other than an alkoxy radical, then $R_1$ and $R_2$ do not simultaneously denote a hydrogen atom;

b) the compounds of formula (II) below:

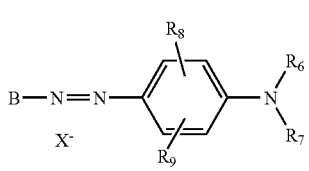

(II)

in which:
$R_6$ represents a hydrogen atom or a $C_1$-$C_4$ alkyl radical, $R_7$ represents a hydrogen atom, an alkyl radical which can be substituted with a —CN radical or with an amino group, a 4'-aminophenyl radical or forms with $R_6$ a heterocycle optionally containing oxygen and/or nitrogen, which can be substituted with a $C_1$-$C_4$ alkyl radical, $R_8$ and $R_9$, which may be identical or different, represent a hydrogen atom, a halogen atom such as bromine, chlorine, iodine or fluorine, a $C_1$-$C_4$ alkyl or $C_1$-$C_4$ alkoxy radical or a —CN radical, $X^-$ represents an anion preferably chosen from chloride, methyl sulphate and acetate, B represents a group chosen from the structures B1 to B6 below:

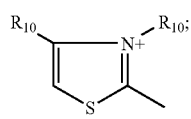
B1

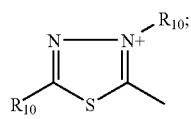
B2

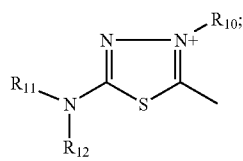
B3

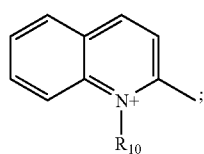
B4

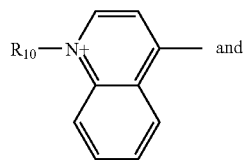
B5 and

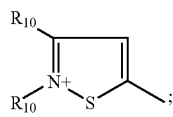
B6 in which $R_{10}$ represents a $C_1$-$C_4$ alkyl radical, $R_{11}$ and $R_{12}$, which may be identical or different, represent a hydrogen atom or a $C_1$-$C_4$ alkyl radical;

c) the compounds of formulae (III) and (III') below:

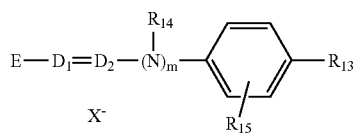
(III)

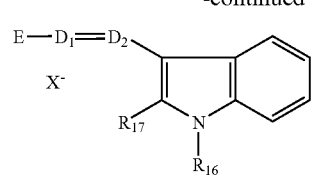
(III')

in which:

$R_{13}$ represents a hydrogen atom, a $C_1$-$C_4$ alkoxy radical, a halogen atom such as bromine, chlorine, iodine or fluorine, or an amino radical, $R_{14}$ represents a hydrogen atom, a $C_1$-$C_4$ alkyl radical or forms, with a carbon atom of the benzene ring, a heterocycle optionally containing oxygen and/or substituted with one or more $C_1$-$C_4$ alkyl groups, $R_{15}$ represents a hydrogen atom or a halogen atom such as bromine, chlorine, iodine or fluorine, $R_{16}$ and $R_{17}$, which may be identical or different, represent a hydrogen atom or a $C_1$-$C_4$ alkyl radical, $D_1$ and $D_2$, which may be identical or different, represent a nitrogen atom or a —CH group, m=0 or 1, it being understood that when $R_{13}$ represents an unsubstituted amino group, then $D_1$ and $D_2$ simultaneously represent a —CH group and m=0, $X^-$ represents an anion preferably chosen from chloride, methyl sulphate and acetate, E represents a group chosen from the structures E1 to E8 below:

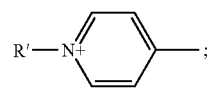
E1

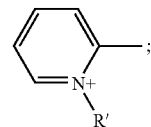
E2

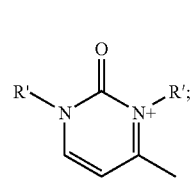
E3

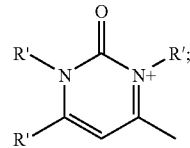
E4

-continued

E5

[Structure: indazole with OH and methyl substituents, N-R', N+-R']

E6

[Structure: benzothiazole with N+-R']

E7

[Structure: pyridine with N+-R'] and

E8

[Structure: triazole with R' groups]

in which R' represents a $C_1$-$C_4$ alkyl radical;

when m=0 and when $D_1$ represents a nitrogen atom, the E can also denote a group of structure E9 below:

E9

[Structure: imidazole with R' groups]

in which R' represents a $C_1$-$C_4$ alkyl radical;

d) the compounds of formula (IV) below:

$$G-N=N-J \quad (IV)$$

in which:

the symbol G represents a group chosen from the structures $G_1$ to $G_3$ below:

$G_1$

[Structure: pyrazolium with $R_{20}$, $R_{21}$, $R_{19}$, $R_{18}$, $X^-$]

$G_2$

[Structure with $R_{20}$, $R_{21}$, Z, $R_{18}$, $X^-$]

$G_3$

[Structure with $R_{23}$, $R_{24}$, K, P, M]

in which structures $G_1$ to $G_3$, $R_{18}$ denotes a $C_1$-$C_4$ alkyl radical, a phenyl radical which can be substituted with a $C_1$-$C_4$ alkyl radical or a halogen atom chosen from chlorine, bromine, iodine and fluorine;

$R_{19}$ denotes a $C_1$-$C_4$ alkyl radical or a phenyl radical;

$R_{20}$ and $R_{21}$, which may be identical or different, represent a $C_1$-$C_4$ alkyl radical, a phenyl radical or together form, in $G_1$, a benzene ring substituted with one or more $C_1$-$C_4$ alkyl, $C_1$-$C_4$ alkoxy or $NO_2$ radicals or together form, in $G_2$, a benzene ring optionally substituted with one or more $C_1$-$C_4$ alkyl, $C_1$-$C_4$ alkoxy or $NO_2$ radicals;

$R_{20}$ can also denote a hydrogen atom;

Z denotes an oxygen or sulphur atom or a group —$NR_{19}$;

M represents a —CH, —CR (R denoting $C_1$-$C_4$ alkyl) or —N⁺$R_{22}$($X^-$)$_r$ group;

K represents a —CH, —CR (R denoting $C_1$-$C_4$ alkyl) or —N⁺$R_{22}$($X^-$)$_r$ group;

P represents a —CH, —CR (R denoting $C_1$-$C_4$ alkyl) or —N⁺$R_{22}$($X^-$)$_r$ group; r denotes zero or 1;

$R_{22}$ represents an $O^-$ anion, a $C_1$-$C_4$ alkoxy radical or a $C_1$-$C_4$ alkyl radical;

$R_{23}$ and $R_{24}$, which may be identical or different, represent a hydrogen atom, a halogen atom chosen from chlorine, bromine, iodine and fluorine, a $C_1$-$C_4$ alkyl or $C_1$-$C_4$ alkoxy radical or an —$NO_2$ radical;

$X^-$ represents an anion preferably chosen from chloride, iodide, methyl sulphate, ethyl sulphate, acetate and perchlorate;

with the proviso that, if $R_{22}$ denotes $O^-$, then r denotes zero;

if K or P or M denote $C_1$-$C_4$ —N⁺-alkyl $X^-$, then $R_{23}$ or $R_{24}$ is other than a hydrogen atom;

if K denotes —N⁺$R_{22}$($X^-$)$_r$, then M=P=—CH, —CR;

if M denotes —N⁺$R_{22}$($X^-$)$_r$, then K=P=—CH, —CR;

if P denotes —N⁺$R_{22}$($X^-$)$_r$, then K=M and denote —CH or —CR;

if Z denotes a sulphur atom with $R_{21}$ denoting $C_1$-$C_4$ alkyl, then $R_{20}$ is other than a hydrogen atom;

if Z denotes —$NR_{22}$ with $R_{19}$ denoting $C_1$-$C_4$ alkyl, then at least one of the radicals $R_{18}$, $R_{20}$ or $R_{21}$ of the group of structure $G_2$ is other than a $C_1$-$C_4$ alkyl radical;

the symbol J represents:

(a) a group of structure $J_1$ below:

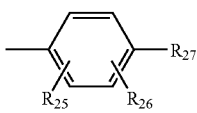

in which structure $J_1$,
$R_{25}$ represents a hydrogen atom, a halogen atom chosen from chlorine, bromine, iodine and fluorine, a $C_1$-$C_4$ alkyl or $C_1$-$C_4$ alkoxy radical, a radical —OH, —NO$_2$, —NHR$_{28}$, —NR$_{29}$R$_{30}$, —NHCO($C_1$-$C_4$) alkyl, or forms with $R_{26}$ a 5- or 6-membered ring which may or may not contain one or more hetero atoms chosen from nitrogen, oxygen and sulphur,
$R_{26}$ represents a hydrogen atom, a halogen atom chosen from chlorine, bromine, iodine and fluorine, a $C_1$-$C_4$ alkyl or $C_1$-$C_4$ alkoxy radical or forms, with $R_{27}$ or $R_{28}$, a 5- or 6-membered ring which may or may not contain one or more hetero atoms chosen from nitrogen, oxygen and sulphur;
$R_{27}$ represents a hydrogen atom, an —OH radical, a radical —NHR$_{28}$ or a radical —NR$_{29}$R$_{30}$;
$R_{28}$ represents a hydrogen atom, a $C_1$-$C_4$ alkyl radical, a $C_1$-$C_4$ monohydroxyalkyl radical, a $C_2$-$C_4$ polyhydroxyalkyl radical or a phenyl radical;
$R_{29}$ and $R_{30}$, which may be identical or different, represent a $C_1$-$C_4$ alkyl radical, a $C_1$-$C_4$ monohydroxyalkyl radical or a $C_2$-$C_4$ polyhydroxyalkyl radical;
(b) a 5- or 6-membered nitrogenous heterocyclic group which can contain other hetero atoms and/or carbonyl groups and which can be substituted with one or more $C_1$-$C_4$ alkyl, amino or phenyl radicals, and in particular a group of structure $J_2$ below:

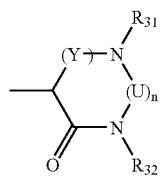

in which structure $J_2$,
$R_{31}$ and $R_{32}$, which may be identical or different, represent a hydrogen atom, a $C_1$-$C_4$ alkyl radical or a phenyl radical;
Y denotes the —CO— radical or the radical

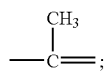

n=0 or 1, with, when n denotes 1, U denoting a —CO— radical.

In the structures (I) to (IV) defined above, the $C_1$-$C_4$ alkyl or alkoxy group preferably denotes methyl, ethyl, butyl, methoxy or ethoxy.

The cationic direct dyes of formulae (I), (II), (III) and (III') which can be used in the dye compositions in accordance with the invention are known compounds and are described, for example, in patent applications WO 95/01772, WO 95/15144 and EP-A-0,714,954. Those of formula (IV) which can be used in the dye compositions in accordance with the invention are known compounds and are described, for example, in patent applications FR-2,189,006, FR-2,285,851 and FR-2,140,205 and its Certificates of Addition.

Among the cationic direct dyes of formula (I) which can be used in the dye compositions in accordance with the invention, mention may be made more particularly of the compounds corresponding to the structures (I1) to (I54) below:

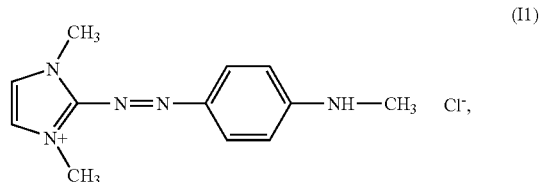

(I1)

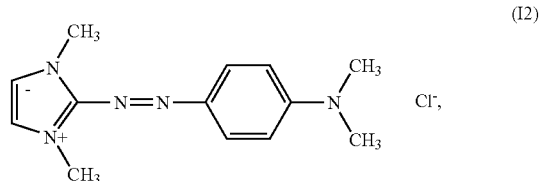

(I2)

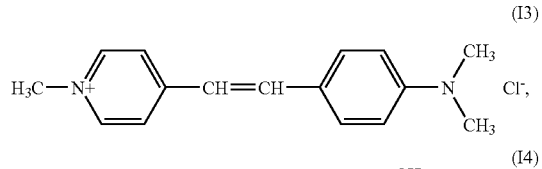

(I3)

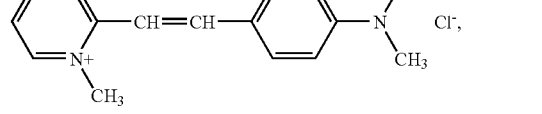

(I4)

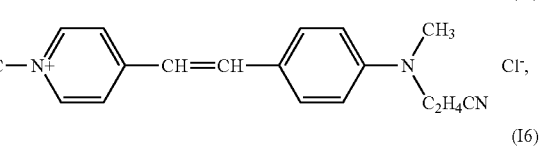

(I5)

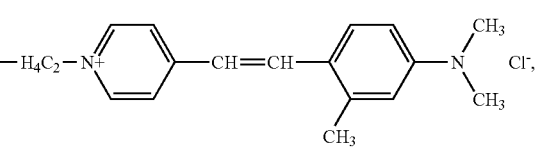

(I6)

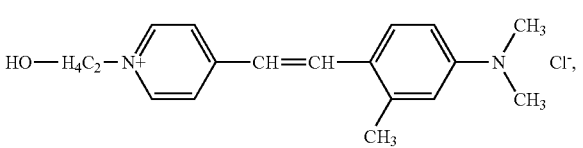

(I7)

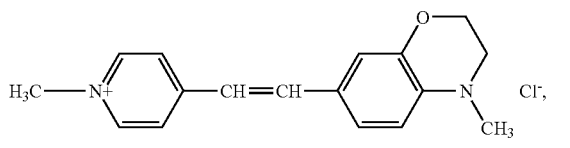

(I8)

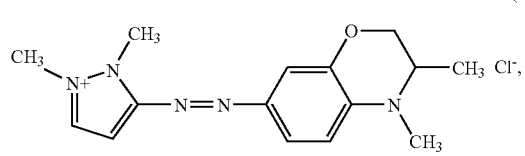

-continued
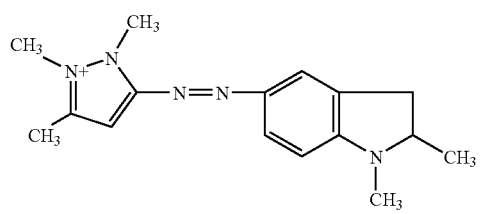
(I9)
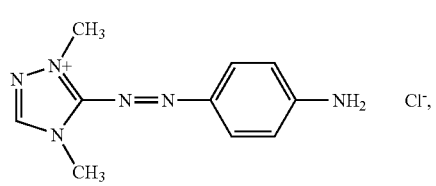
(I10)
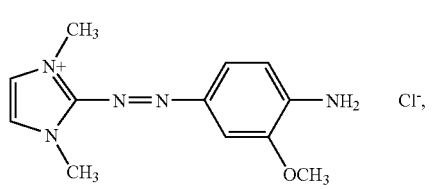
(I11)
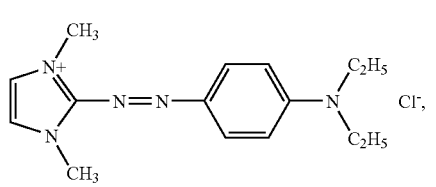
(I12)
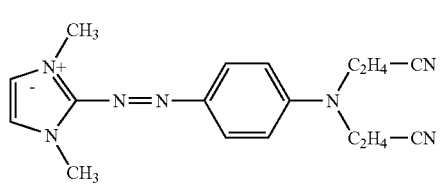
(I13)
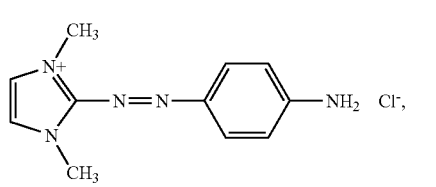
(I14)
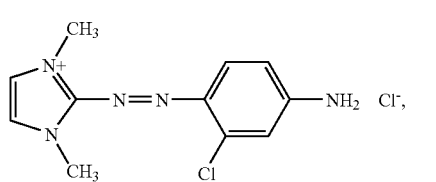
(I15)
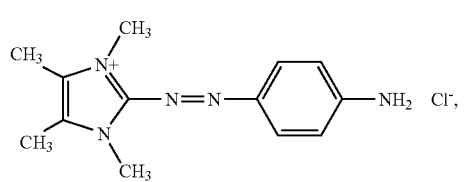
(I16)
-continued
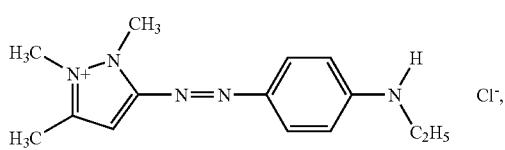
(I17)
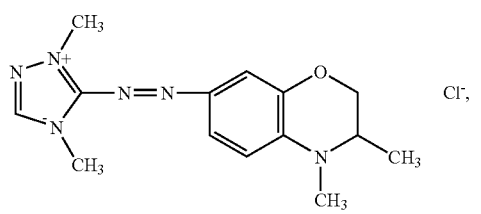
(I18)
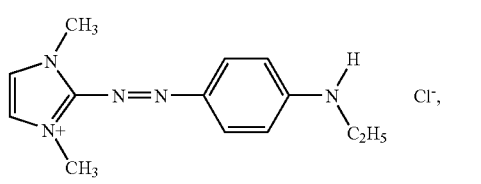
(I19)
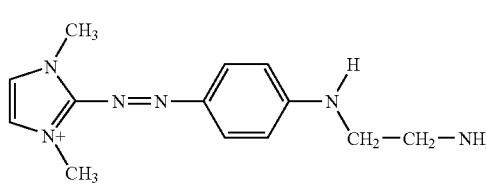
(I20)
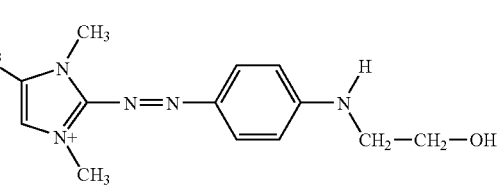
(I21)
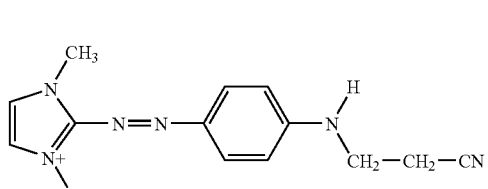
(I22)
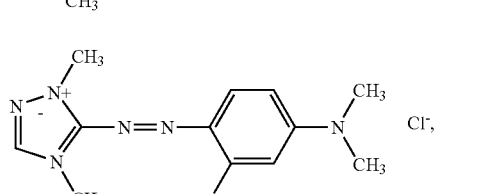
(I23)
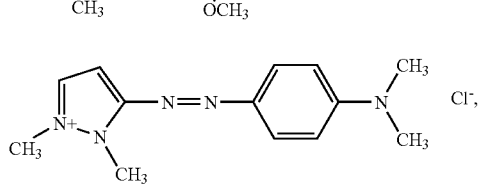
(I24)

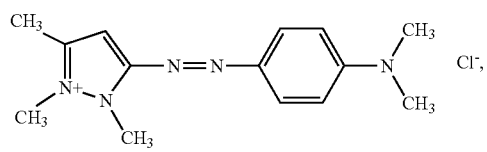 (I25)
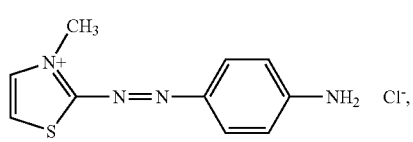 (I26)
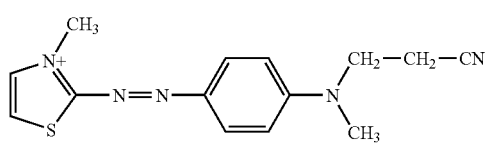 (I27)
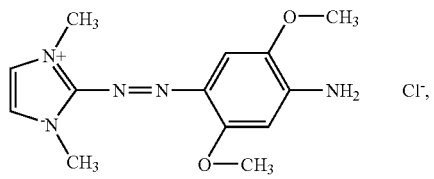 (I28)
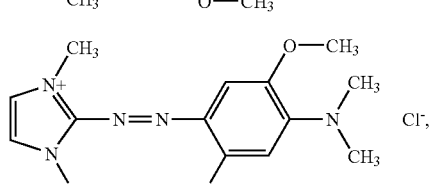 (I29)
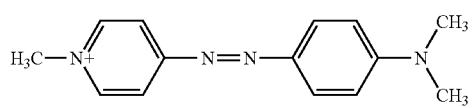 (I30)
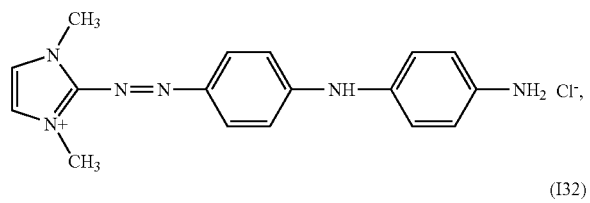 (I31)
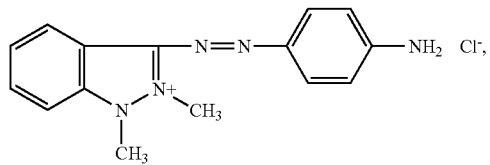 (I32)
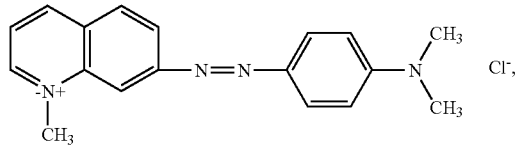 (I33)
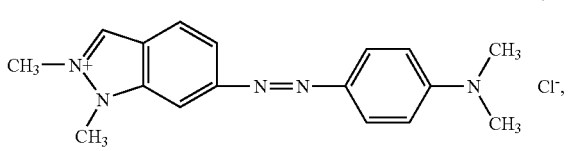 (I34)
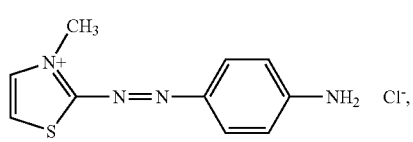 (I35)
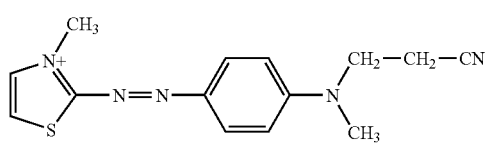 (I36)
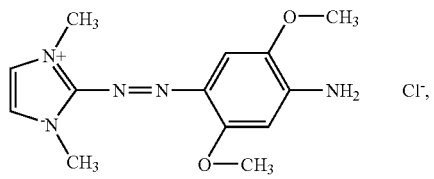 (I37)
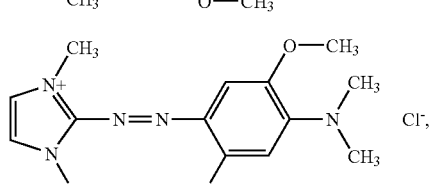 (I38)
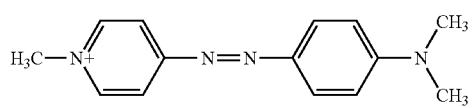 (I39)
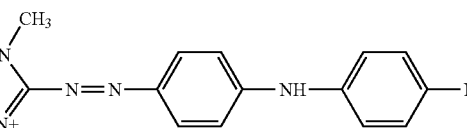 (I40)
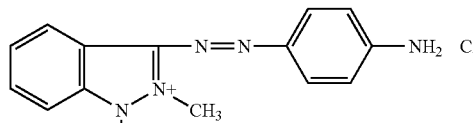 (I41)
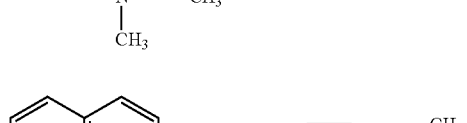 (I42)

(I43) 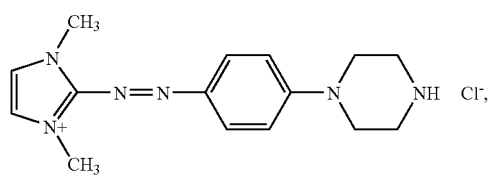

(I44) 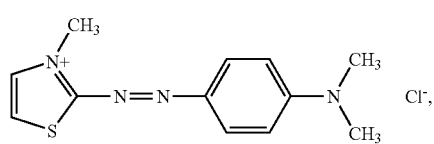

(I45) 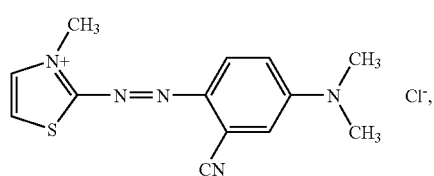

(I46) 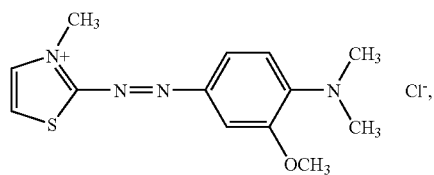

(I47) 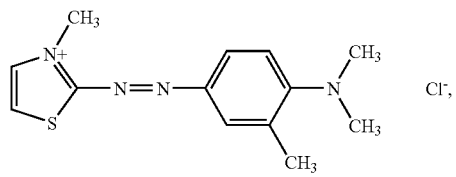

(I48) 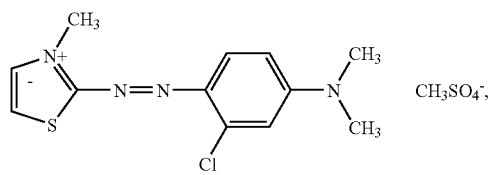

(I49) 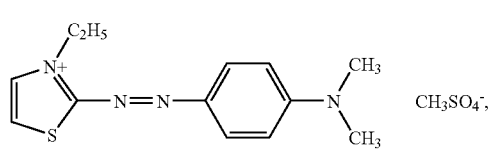

(I50) 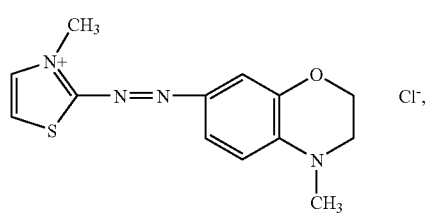

(I51) 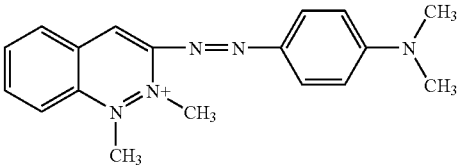

(I52) 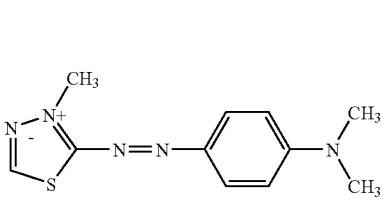

(I53) 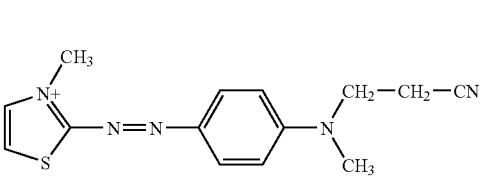

(I54) 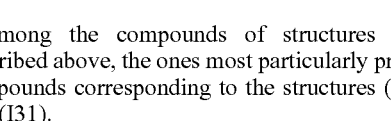

Among the compounds of structures (I1) to (I54) described above, the ones most particularly preferred are the compounds corresponding to the structures (I1), (I2), (I14) and (I31).

Among the cationic direct dyes of formula (II) which can be used in the dye compositions in accordance with the invention, mention may be made more particularly of the compounds corresponding to the structures (II1) to (II9) below:

(II1) 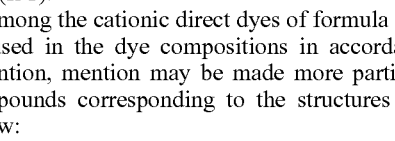

(II2) 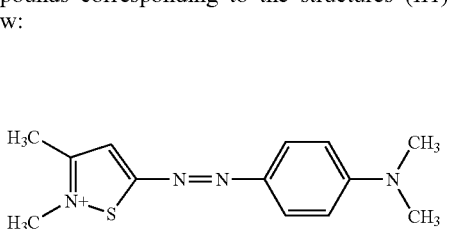

(II3) 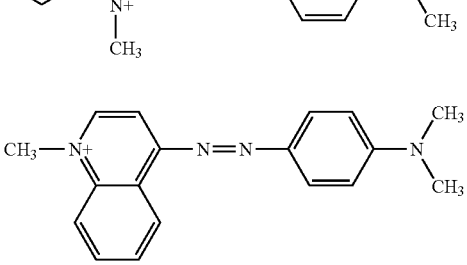

-continued
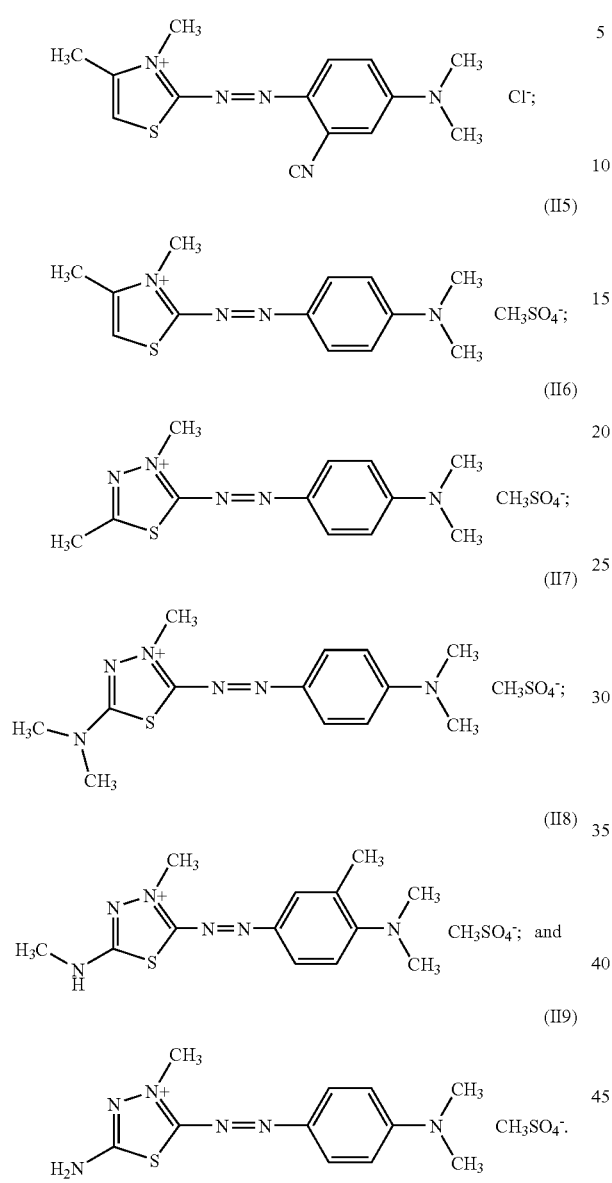
Among the cationic direct dyes of formula (III) which can be used in the dye compositions in accordance with the invention, mention may be made more particularly of the compounds corresponding to the structures (III1) to (III18) below:
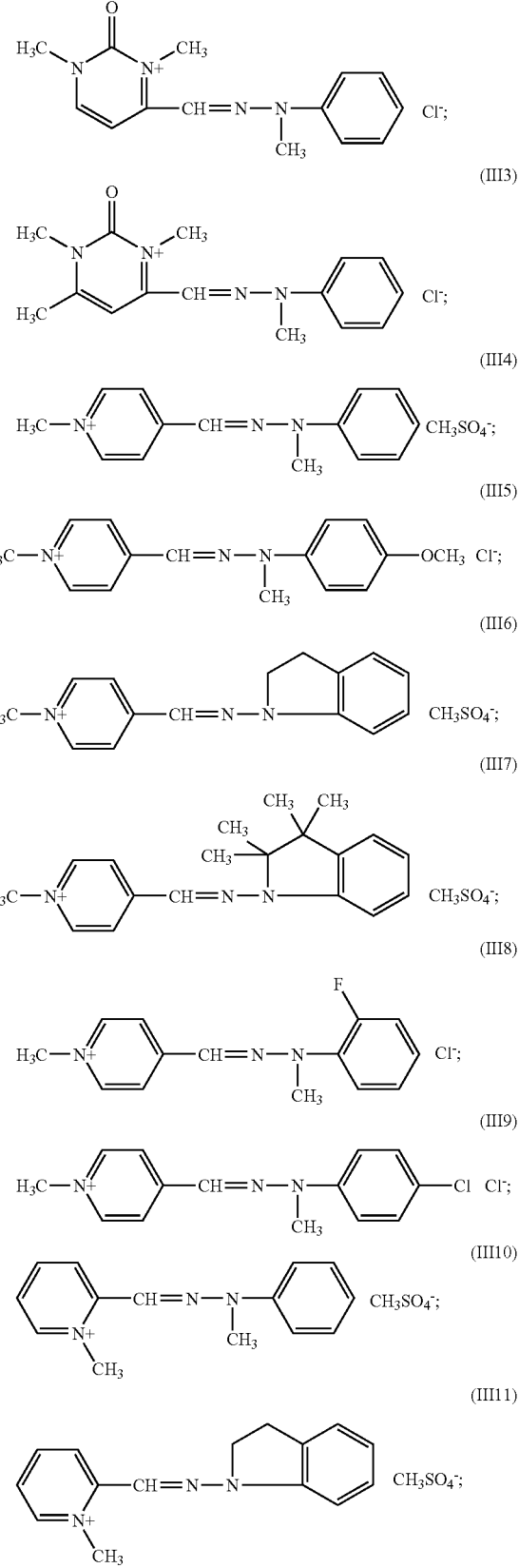
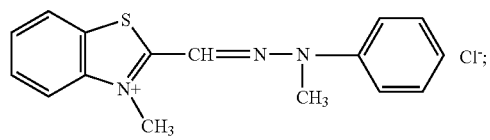
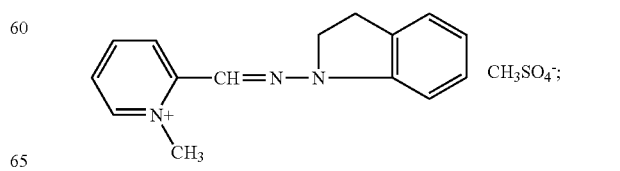

-continued

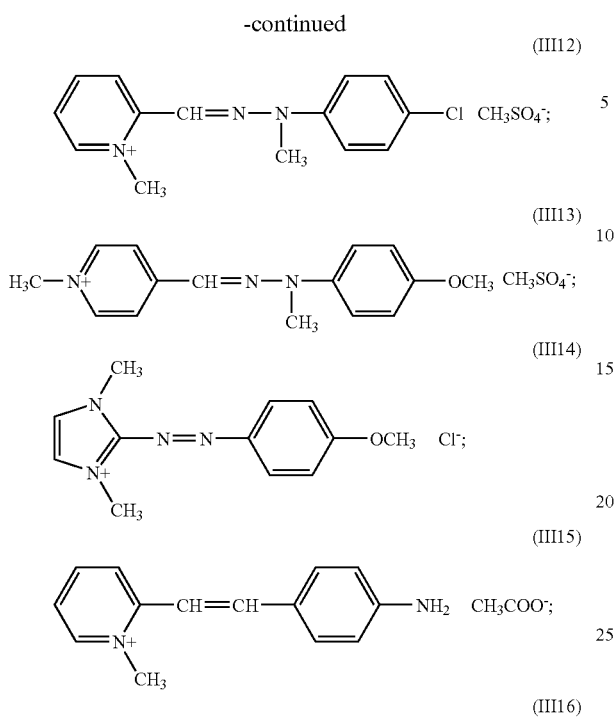

Among the specific compounds of structures (III1) to (III18) described above, the ones most particularly preferred are the compounds corresponding to the structures (III4), (III5) and (III13).

Among the cationic direct dyes of formula (III') which can be used in the dye compositions in accordance with the invention, mention may be made more particularly of the compounds corresponding to the structures (III'1) to (III'3) below:

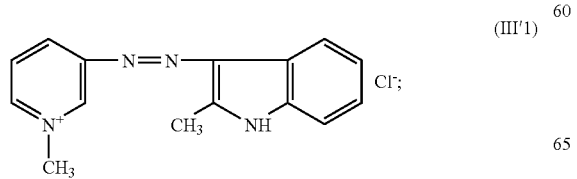

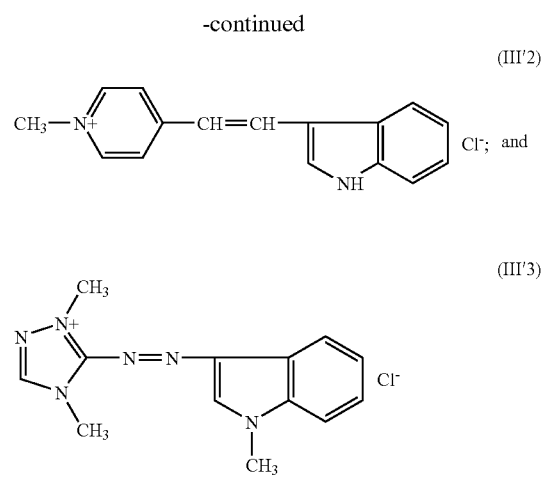

Among the cationic direct dyes of formula (IV) which can be used in the dye compositions in accordance with the invention, mention may be made more particularly of the compounds of structures $(IV)_1$ to $(IV)_{77}$ below:

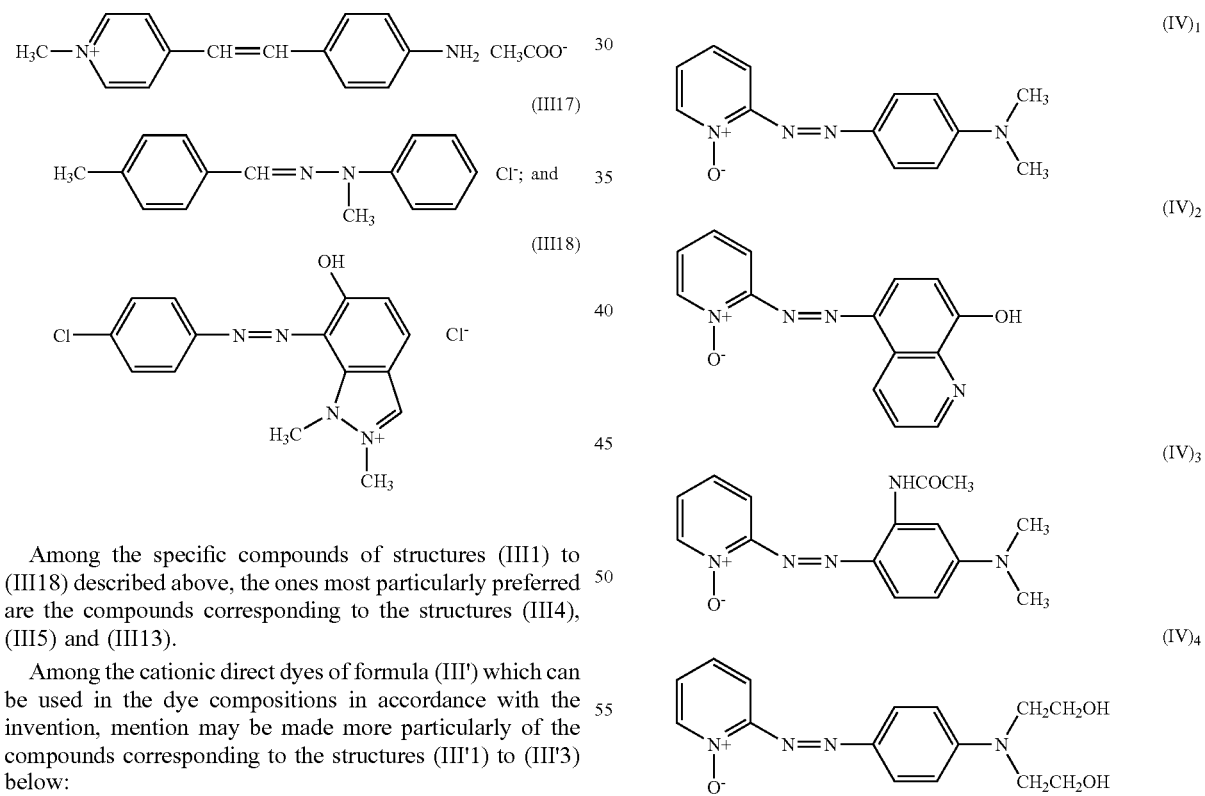

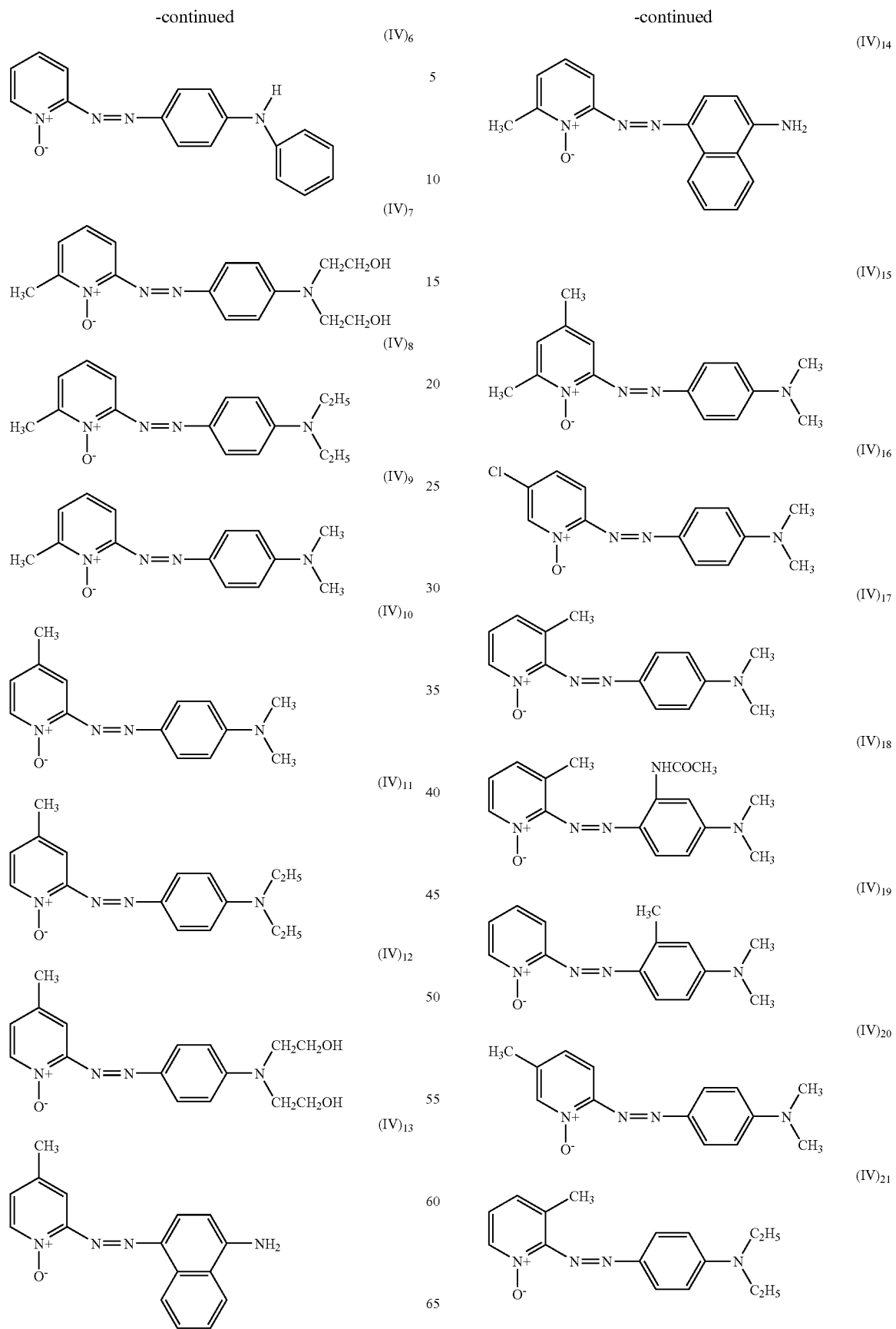

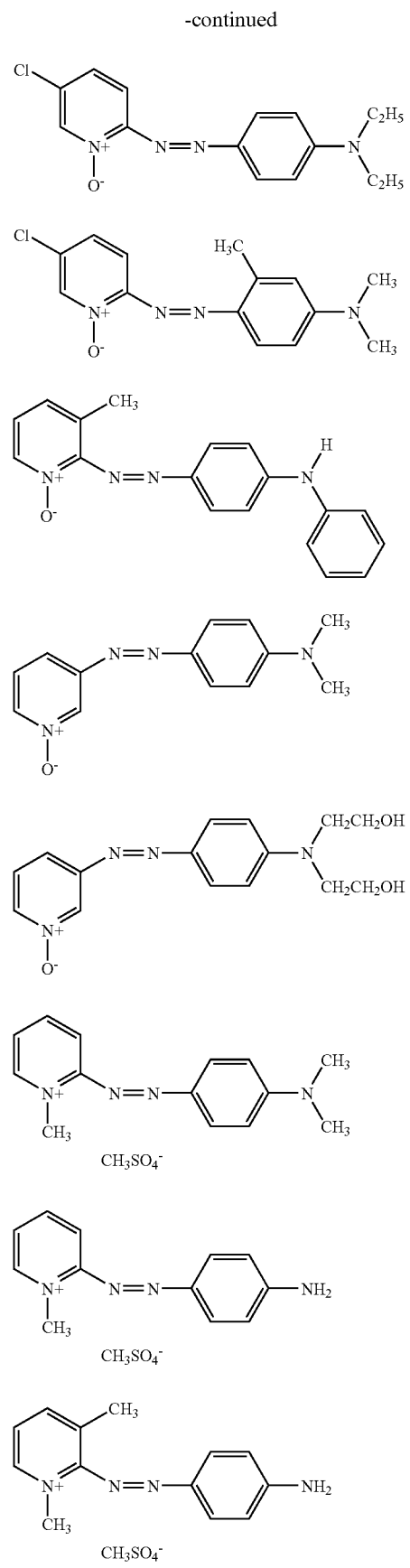

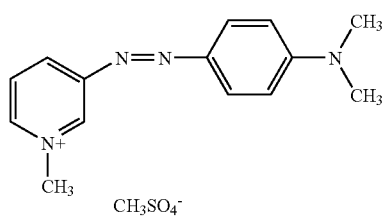
(IV)37
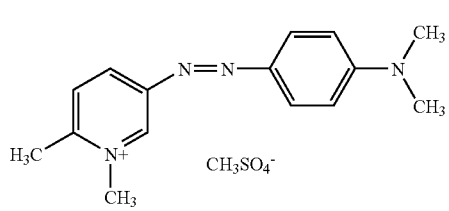
(IV)38
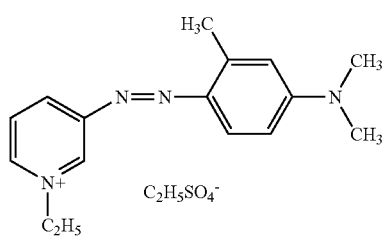
(IV)39
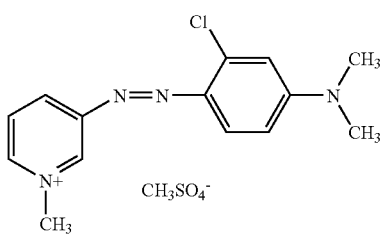
(IV)40
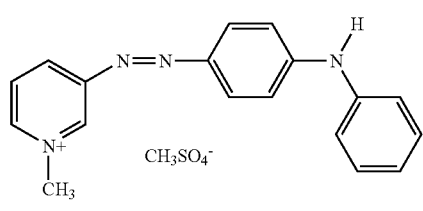
(IV)41
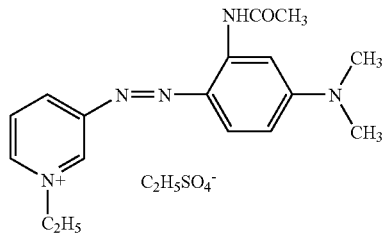
(IV)42
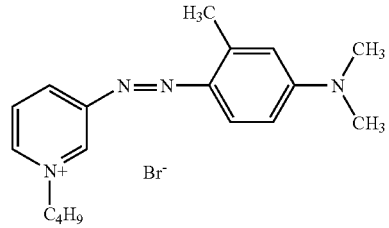
(IV)43
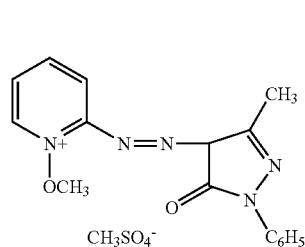
(IV)44
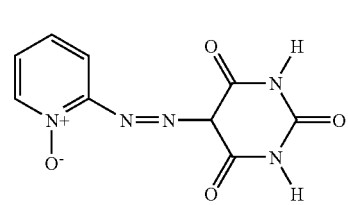
(IV)45
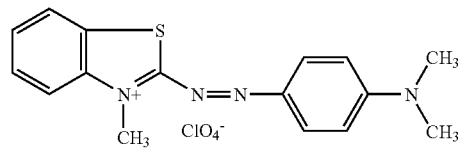
(IV)46
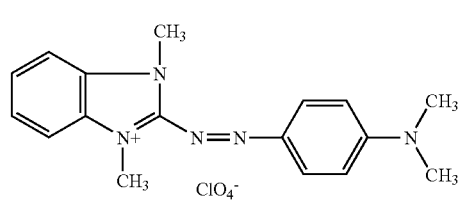
(IV)47
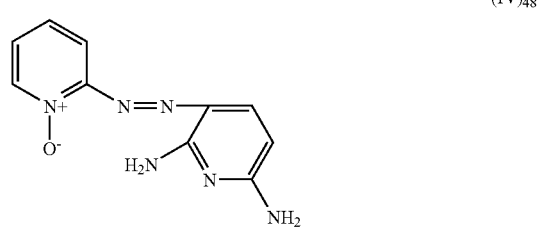
(IV)48
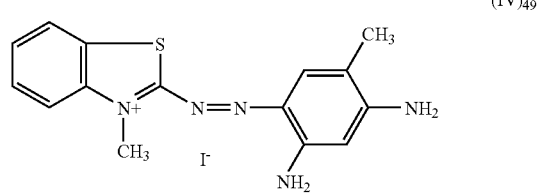
(IV)49

-continued
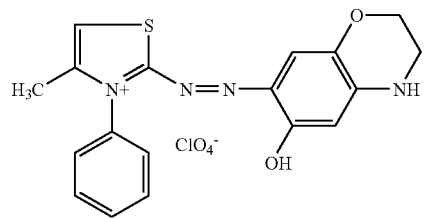 (IV)₅₀
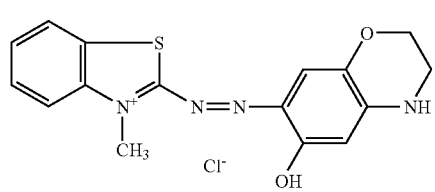 (IV)₅₁
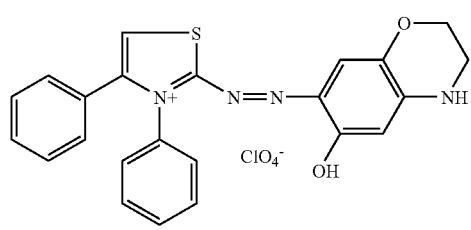 (IV)₅₂
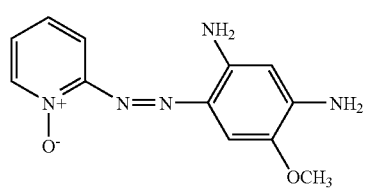 (IV)₅₃
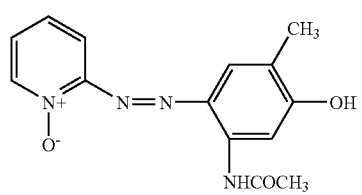 (IV)₅₄
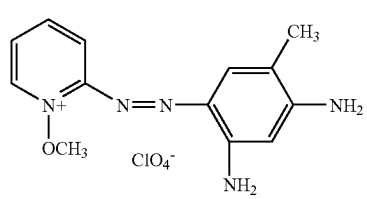 (IV)₅₅
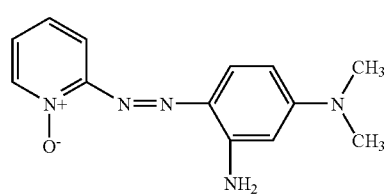 (IV)₅₆
-continued
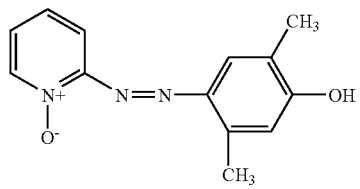 (IV)₅₇
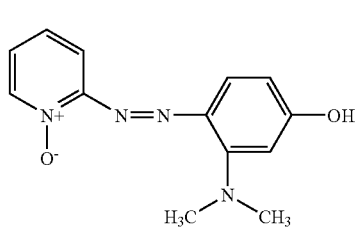 (IV)₅₈
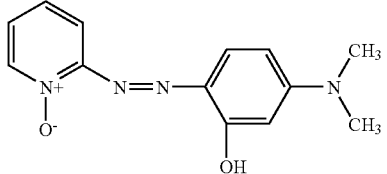 (IV)₅₉
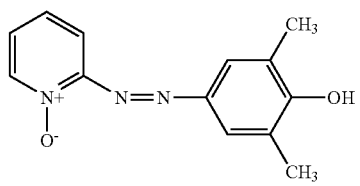 (IV)₆₀
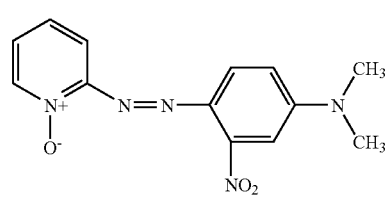 (IV)₆₁
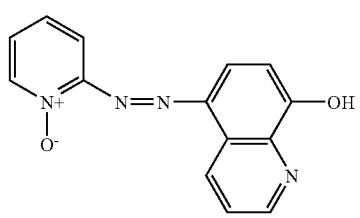 (IV)₆₂
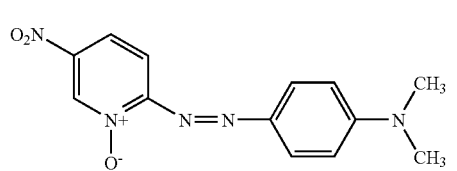 (IV)₆₃

(IV)₆₄ 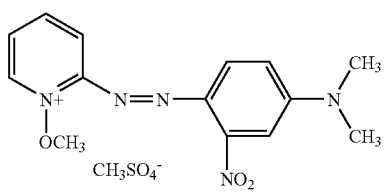
(IV)₆₅ 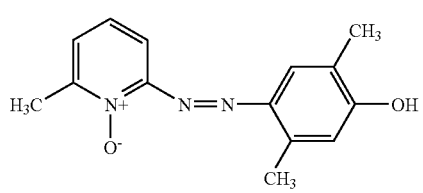
(IV)₆₆ 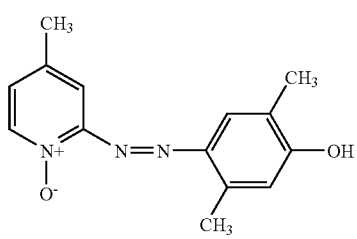
(IV)₆₇ 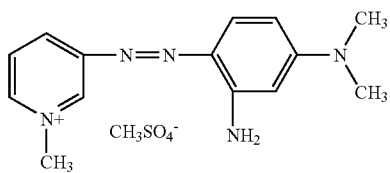
(IV)₆₈ 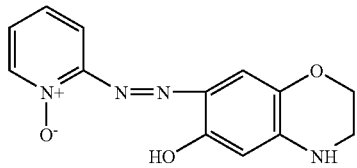
(IV)₆₉ 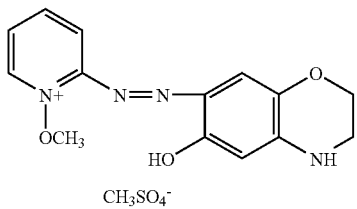
(IV)₇₀ 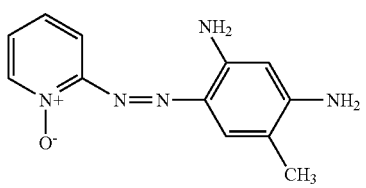
(IV)₇₁ 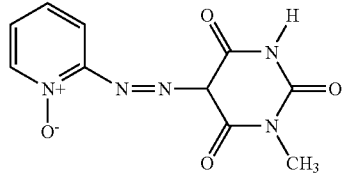
(IV)₇₂ 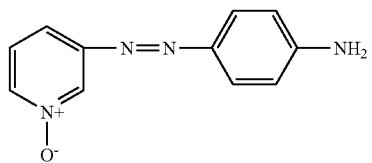
(IV)₇₃ 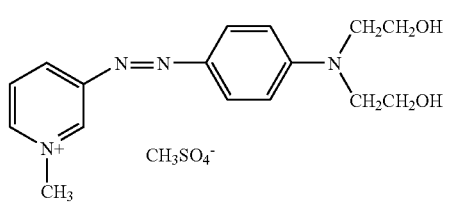
(IV)₇₄ 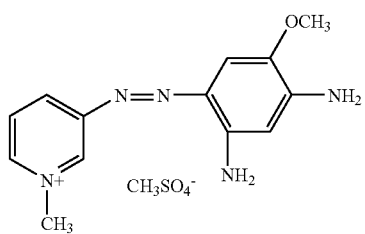
(IV)₇₅ 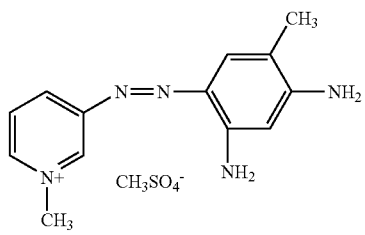
(IV)₇₆ 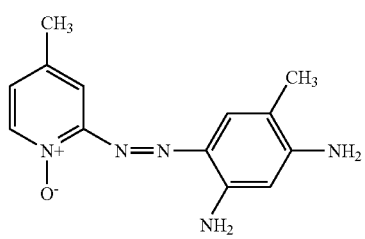
(IV)₇₇ 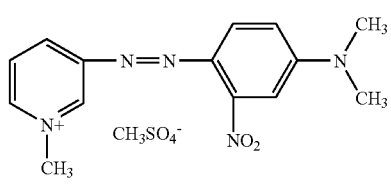

The cationic direct dye(s) used according to the invention preferably represent(s) from 0.001 to 10% by weight approximately relative to the total weight of the dye composition and even more preferably from 0.005 to 5% by weight approximately relative to this weight.

(ii) The thickening polymer which can be used according to the present invention is chosen from the group consisting of:

(ii)$_1$—nonionic amphiphilic polymers comprising at least one hydrophilic unit and at least one unit containing a fatty chain.;

(ii)$_2$—anionic amphiphilic polymers comprising at least one hydrophilic unit and at least one unit containing a fatty chain;

(ii)$_3$—cationic amphiphilic polymers comprising at least one hydrophilic unit and at least one unit containing a fatty chain.

The nonionic amphiphilic polymers comprising at least one hydrophilic unit and at least one unit containing a fatty chain (ii)$_1$, used according to the invention, are preferably chosen from:

(ii)$_1$(a) celluloses modified with groups comprising at least one fatty chain; mention may be made, by way of example, of:

hydroxyethylcelluloses modified with groups comprising at least one fatty chain, such as alkyl, arylalkyl or alkylaryl groups or mixtures thereof, and in which the alkyl groups are preferably $C_8$-$C_{22}$, such as the product Natrosol Plus Grade 330 CS ($C_{16}$ alkyls) sold by the company Aqualon, or the product Bermocoll EHM 100 sold by the company Berol Nobel, hydroxyethylcelluloses modified with groups comprising at least one polyalkylene glycol alkylphenyl ether group, such as the product Amercell Polymer HM-1500 (polyethylene glycol (15) nonylphenyl ether) sold by the company Amerchol.

(ii)$_1$(b) hydroxypropylguars modified with groups comprising at least one fatty chain, such as the product Esaflor HM 22 ($C_{22}$ alkyl chain) sold by the company Lamberti, and the products Miracare XC95-3 ($C_{14}$ alkyl chain) and RE205-1 ($C_{20}$ alkyl chain) sold by the company Rhône-Poulenc.

(ii)$_1$(c) polyurethane ethers comprising at least one fatty chain such as $C_8$-$C_{30}$ alkyl or alkenyl groups, for instance the products Dapral T 210 and Dapral T 212 sold by the company Akzo.

(ii)$_1$(d) copolymers of vinylpyrrolidone and of hydrophobic monomers containing a fatty chain;

mention may be made, by way of example, of:

the products Antaron V216 or Ganex V216 (vinylpyrrolidone/hexadecene copolymer) sold by the company I.S.P.

the products Antaron V220 or Ganex V220 (vinylpyrrolidone/eicosene copolymer) sold by the company I.S.P.

(ii)$_1$(e) copolymers of $C_1$-$C_6$ alkyl methacrylates or acrylates and of amphiphilic monomers comprising at least one fatty chain, such as, for example, the oxyethylated methyl methacrylate/stearyl acrylate copolymer sold by the company Goldschmidt under the name Antil 208.

(ii)$_1$(f) copolymers of hydrophilic methacrylates or acrylates and of hydrophobic monomers comprising at least one fatty chain, such as, for example, the polyethylene glycol methacrylate/lauryl methacrylate copolymer.

The anionic amphiphilic polymers (ii)$_2$ can be chosen from those:

(ii)$_2$(a) comprising at least one hydrophilic unit and at least one allyl ether unit containing a fatty chain, and preferably from those in which the hydrophilic unit comprising an unsaturated ethylenic anionic monomer, more particularly of a vinylcarboxylic acid and most particularly of an acrylic acid, a methacrylic acid or mixtures thereof, and in which the allyl ether unit containing a fatty chain corresponds to the monomer of formula (V) below:

$$CH_2=CR'CH_2O\ B_nR \qquad (V)$$

in which R' denotes H or $CH_3$, B denotes an ethylenoxy radical, n is zero or denotes an integer ranging from 1 to 100, R denotes a hydrocarbon-based radical chosen from alkyl and cycloalkyl radicals comprising from 8 to 30 carbon atoms, preferably 10 to 24 and even more particularly from 12 to 18 carbon atoms, and most particularly a $C_{10}$-$C_{24}$ alkyl radical.

One unit of formula (V) which is more particularly preferred according to the present invention is a unit in which R' denotes H, n is equal to 10 and R denotes a stearyl ($C_{18}$) radical.

Anionic amphiphilic polymers of this type are described and prepared according to an emulsion polymerization process in patent EP-0,216,479 B2.

Among the said anionic amphiphilic polymers cited (ii)$_2$ (a) it is particularly preferred according to the invention to use the polymers formed from 20 to 60% by weight of acrylic acid and/or methacrylic acid, from 5 to 60% by weight of lower alkyl (meth)acrylates, from 2 to 50% by weight of allyl ether containing a fatty chain of formula (I), and from 0 to 1% by weight of a crosslinking agent which is a well known copolymerizable polyethylenic unsaturated monomer, such as diallyl phthalate, allyl (meth)acrylate, divinylbenzene, (poly)ethylene glycol dimethacrylate and methylenebisacrylamide.

Among the latter polymers, the ones most particularly preferred are the crosslinked terpolymers of methacrylic acid, of ethyl acrylate, of polyethylene glycol (10 EO) stearyl ether (Steareth-10), in particular those sold by the company Allied Colloids under the names Salcare SC 80 and Salcare SC 90 which are aqueous 30% emulsions of a crosslinked terpolymer of methacrylic acid, of ethyl acrylate and of Steareth-10 allyl ether (40/50/10).

The anionic amphiphilic polymers (ii)$_2$ can also be chosen from those:

(ii)$_2$(b) comprising at least one hydrophilic unit of unsaturated olefinic carboxylic acid type, and at least one unit containing a fatty chain exclusively of ($C_{10}$-$C_{30}$) alkyl ester of unsaturated carboxylic acid type, and preferably from those in which the hydrophilic unit of unsaturated olefinic-carboxylic acid type corresponds to the monomer of formula (VI) below:

$$CH_2=\underset{R^1}{\underset{|}{C}}-\underset{O}{\overset{\|}{C}}-OH \qquad (VI)$$

in which formula $R^1$ denotes H or $CH_3$ or $C_2H_5$, i.e. acrylic acid, methacrylic acid or ethacrylic acid units, and in which the unit containing a fatty chain of ($C_{10}$-$C_{30}$)alkyl ester of unsaturated carboxylic acid type corresponds to the monomer of formula (VII) below:

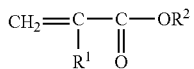 (VII)

in which formula $R^1$ denotes H or $CH_3$ or $C_2H_5$ (i.e. acrylate, methacrylate or ethylacrylate units) and preferably H (acrylate units) or $CH_3$ (methacrylate units), $R^2$ denoting a $C_{10}$-$C_{30}$ alkyl and preferably $C_{12}$-$C_{22}$ alkyl radical.

($C_{10}$-$C_{30}$)alkyl esters of unsaturated carboxylic acids in accordance with the invention comprise, for example, lauryl acrylate, stearyl acrylate, decyl acrylate, isodecyl acrylate, dodecyl acrylate and the corresponding methacrylates, lauryl methacrylate, stearyl methacrylate, decyl methacrylate, isodecyl methacrylate and dodecyl methacrylate.

Anionic amphiphilic polymers of this type $(ii)_2(b)$ are described and prepared, for example, according to U.S. Pat. Nos. 3,915,921 and 4,509,949.

Anionic amphiphilic polymers $(ii)_2(b)$ which can be used in the context of the present invention can more particularly denote polymers formed from a mixture of monomers comprising:

(i) essentially acrylic acid and an ester of formula (VII) described above in which $R^1$ denotes H or $CH_3$, $R^2$ denoting an alkyl radical containing from 12 to 22 carbon atoms, and a crosslinking agent, such as, for example, those comprising 95 to 60% by weight of acrylic acid (hydrophilic unit), 4 to 40% by weight of $C_{10}$-$C_{30}$ alkyl acrylate (unit containing a fatty chain) and 0 to 6% by weight of crosslinking polymerizable monomer, or 98 to 96% by weight of acrylic acid (hydrophilic unit), 1 to 4% by weight of $C_{10}$-$C_{30}$ alkyl acrylate (unit containing a fatty chain) and 0.1 to 0.6% by weight of crosslinking polymerizable monomer, (ii) essentially acrylic acid and lauryl methacrylate, such as the polymer formed from 66% by weight of acrylic acid and 34% by weight of lauryl methacrylate.

The said crosslinking agent is a monomer containing a group $CH_2=C<$ with at least one other polymerizable group whose unsaturated bonds are not conjugated to each other. Mention may be made in particular of polyallyl ethers such as, in particular, polyallylsucrose and polyallylpentaerythritol.

Among the said polymers cited in class $(ii)_2(b)$, the ones most particularly preferred according to the present invention are the products sold by the company Goodrich under the trade names Pemulen TR1, Pemulen TR2, Carbopol 1382 and even more preferably Pemulen TR1 and the product sold by the company S.E.P.C. under the name Coatex SX.

The cationic amphiphilic polymers $(ii)_3$ used according to the invention are preferably chosen from quaternized cellulose derivatives and polyacrylates containing amino side groups.

The quaternized cellulose derivatives are, in particular, $(ii)_3(a)$ quaternized celluloses modified with groups comprising at least one fatty chain, such as alkyl, arylalkyl or alkylaryl groups comprising at least 8 carbon atoms, or mixtures thereof, $(ii)_3(b)$ quaternized hydroxyethylcelluloses modified with groups comprising at least one fatty chain, such as alkyl, arylalkyl or alkylaryl groups comprising at least 8 carbon atoms, or mixtures thereof.

The polyacrylates containing amino side groups $(ii)_3(c)$, which may or may not be quaternized, contain, for example, hydrophobic groups such as Steareth-20 [polyoxyethylenated (20) stearyl alcohol].

The alkyl radicals borne by the above quaternized celluloses or hydroxycelluloses preferably comprise from 8 to 30 carbon atoms.

The aryl radicals preferably denote phenyl, benzyl, naphthyl or anthryl groups.

As examples of quaternized alkylhydroxyethyl-celluloses containing $C_8$-$C_{30}$ fatty chains, mention may be made of the products Quatrisoft LM200, Quatrisoft LM-X529-18-A, Quatrisoft LM-X529-18-B ($C_{12}$ alkyl) and Quatrisoft LM-X529-8 ($C_{18}$ alkyl) sold by the company Amerchol and the products Crodacel QM, Crodacel QL ($C_{12}$ alkyl) and Crodacel QS ($C_{18}$ alkyl) sold by the company Croda.

As examples of polyacrylates containing amino side chains, mention may be made of the polymers 8781-124B or 9492-103 from the company National Starch.

It is more particularly preferred, according to the present invention, to use the amphiphilic polymers of nonionic type $(ii)_1$ and of anionic type $(ii)_2$ described above and even more particularly the amphiphilic polymers of class $(ii)_1(a)$ and $(ii)_2(c)$ and of class $(ii)_2(a)$ and $(ii)_2(b)$.

The amphiphilic thickening polymers of nonionic, anionic or cationic type used in the compositions of the present invention are preferably present in a proportion of from 0.01 to 10% by weight approximately, in particular in a proportion of from 0.1 to 5% by weight approximately, relative to the total weight of the dye composition applied to the keratin fibres.

The medium which is suitable for dyeing (or support) generally comprising water or of a mixture of water and at least one organic solvent to dissolve the compounds which would not be sufficiently water-soluble. As organic solvents, mention may be made, for example, of $C_1$-$C_4$ lower alkanols such as ethanol and isopropanol; aromatic alcohols such as benzyl alcohol, as well as similar products and mixtures thereof.

The solvents can be present in proportions preferably of between 1 and 40% by weight approximately relative to the total weight of the dye composition, and even more preferably between 5 and 30% by weight approximately.

The pH of the dye composition-in accordance with the invention is generally approximately between 2 and 11 and preferably approximately between 5 and 10. It can be adjusted to the desired value using acidifying or basifying agents usually used for dyeing keratin fibres.

Among the acidifying agents, mention may be made, by way of example, of inorganic or organic acids such as hydrochloric acid, orthophosphoric acid, sulphuric acid, carboxylic acids such as acetic acid, tartaric acid, citric acid and lactic acid, and sulphonic acids.

Among the basifying agents, mention may be made, by way of example, of aqueous ammonia, alkaline carbonates, alkanolamines such as mono-, di- and triethanolamine and derivatives thereof, sodium hydroxide, potassium hydroxide and the compounds of formula (VIII) below:

 (VIII)

in which W is a propylene residue optionally substituted with a hydroxyl group or a $C_1$-$C_6$ alkyl radical; $R_{33}$, $R_{34}$, $R_{35}$ and $R_{36}$, which may be identical or different, represent a hydrogen atom or a $C_1$-$C_6$ alkyl or $C_1$-$C_6$ hydroxyalkyl radical.

In addition to the cationic direct dye(s) (i) defined above, the dye composition in accordance with the invention can contain one or more additional direct dyes which can be chosen, for example, from nitrobenzene dyes, anthraquinone dyes, naphthoquinone dyes, triarylmethane dyes, xanthene dyes and azo dyes which are non-cationic.

When it is intended for oxidation dyeing, the dye composition in accordance with the invention contains, in addition to the cationic direct dye(s) (i), one or more oxidation bases chosen from the oxidation bases conventionally used for oxidation dyeing and among which mention may be made in particular of para-phenylenediamines, bis(phenyl)alkylenediamines, para-aminophenols, ortho-aminophenols and heterocyclic bases.

When they are used, the oxidation base(s) preferably represent(s) from 0.0005 to 12% by weight approximately relative to the total weight of the dye composition, and even more preferably from 0.005 to 6% by weight approximately relative to this weight.

When it is intended for oxidation dyeing, the dye composition in accordance with the invention can also contain, in addition to the cationic direct dye (i) and the thickening polymer (ii) as well as the oxidation bases, one or more couplers so as to modify the shades obtained or to enrich them with glints, by using the cationic direct dye(s) (i) and the oxidation base(s).

The couplers which can be used in the dye composition in accordance with the invention can be chosen from the couplers used conventionally in oxidation dyeing and among which mention may be made in particular of meta-phenylenediamines, meta-aminophenols, meta-diphenols and heterocyclic couplers.

When it is (they are) present, the couplers) preferably represent(s) from 0.0001 to 10% by weight approximately relative to the total weight of the dye composition, and even more preferably from 0.005 to 5% by weight approximately relative to this weight.

The dye composition in accordance with the invention can also contain various adjuvants conventionally used in compositions for dyeing the hair, such as antioxidants, penetrating agents, sequestering agents, fragrances, buffers, dispersing agents, surfactants, film-forming agents, ceramides, preserving agents, screening agents and opacifiers.

Needless to say, a person skilled in the art will take care to select this (these) optional complementary compound(s) such that the advantageous properties intrinsically associated with the dye composition in accordance with the invention are not, or are not substantially, adversely affected by the addition(s) envisaged.

The dye composition according to the invention can be in various forms, such as in the form of liquids, shampoos, creams or gels or any other form which is suitable for dyeing keratin fibres, and in particular human hair. It can be obtained by mixing, at the time of use, a composition, which may be pulverulent, containing the cationic direct dye(s) with a composition containing the specific thickening polymer.

When the combination of the cationic direct dye (i) and the thickening polymer (ii) according to the invention is used in a composition intended for oxidation dyeing (in which case one or more oxidation bases are used, optionally in the presence of one or more couplers) or when it is used in a composition intended for lightening direct dyeing, then the dye composition in accordance with the invention also comprises at least one oxidizing agent chosen, for example, from hydrogen peroxide, urea peroxide, alkali metal bromates, persalts such as perborates and persulphates, and enzymes such as peroxidases, lactases and two-electron oxidoreductases. It is particularly preferred to use hydrogen peroxide or enzymes.

Another subject of the invention is a process for dyeing keratin fibres, and in particular human keratin fibres such as the hair, using the dye composition as defined above.

According to a first variant of this dyeing process in accordance with the invention, at least one dye composition as defined above is applied to the fibres, for a period which is sufficient to develop the desired coloration, after which the fibres are rinsed, optionally washed with shampoo, rinsed again and dried.

The time required to develop the coloration on the keratin fibres is generally between 3 and 60 minutes and even more specifically between 5 and 40 minutes.

According to a second variant of this dyeing process in accordance with the invention, at least one dye composition as defined above is applied to the fibres, for a period which is sufficient to develop the desired coloration, without final rinsing.

According to one specific embodiment of this dyeing process, and when the dye composition in accordance with the invention comprises at least one oxidation base and at least one oxidizing agent, the dyeing process comprises a first step which consists in separately storing, on the one hand, a composition (A1) comprising, in a medium which is suitable for dyeing, at least one cationic direct dye (i) as defined above and at least one oxidation base, and, on the other hand, a composition (B1) comprising, in a medium which is suitable for dyeing, at least one oxidizing agent, and then in mixing them together at the time of use, after which this mixture is applied to the keratin fibres, the composition (A1) or the composition (B1) containing the thickening polymer (ii) as defined above.

According to another specific embodiment of this dyeing process, and when the dye composition in accordance with the invention comprises at least one oxidizing agent, the dyeing process comprises a first step which consists in separately storing, on the one hand, a composition (A2) comprising, in a medium which is suitable for dyeing, at least one cationic direct dye (i) as defined above, and, on the other hand, a composition (B2) comprising, in a medium which is suitable for dyeing, at least one oxidizing agent, and then in mixing them together at the time of use, after which this mixture is applied to the keratin fibres, the composition (A2) or the composition (B2) containing the thickening polymer as defined above.

Another subject of the invention is a multi-compartment dyeing device or dyeing "kit" or any other multi-compartment packaging system, a first compartment of which comprises the composition (A1) or (A2) as defined above and a second compartment of which comprises the composition (B1) or (B2) as defined above. These devices can be equipped with means for dispensing the desired mixture onto the hair, such as the devices described in patent FR 2,586,913 in the name of the Applicant.

The examples which follow are intended to illustrate the invention without, however, limiting its scope.

EXAMPLES

Examples 1 to 3

The three direct dyeing compositions given in the tsble below were prepared:

(All Contents Expressesd in Grams)

|  | Example 1 | Example 2 | Example 3 |
|---|---|---|---|
| Cationic direct dye of formula (I1) | 0.2 | | |
| Cationic direct dye of formula (I14) | | 0.2 | |
| Cationic direct dye of formula (IV27) | | | 0.1 |
| Diurethane (HMD) of oxyethylenated (66 EO) and oxypropylenated (14 PO) $C_{16}$-$C_{18}$ alcohols, sold under the name Dapral T212 by the company Akzo | 1.0 AM* | | |
| Methacrylic acid/ethyl acrylate/Steareth 10 allyl ether crosslinked terpolymer sold as a 30% by weight emulsion under the name Salcare SC90 by the company Allied Colloid | | 1.0 AM* | |
| Acrylic acid/$C_{10}$-$C_{30}$ alkyl acrylate crosslinked copolymer sold under the name Pemulen TR1 by the company Goodrich | | | 1.0 AM* |
| Ethanol | 10 | 10 | 10 |
| 2-Amino-2-methyl-1-propanol qs | pH 9 | pH 9 | pH 9 |
| Demineralized water qs | 100 | 100 | 100 |

AM* denotes active material

The above compositions were each applied for 30 minutes to locks of natural grey hair containing 90% white hairs. The locks of hair were then rinsed, washed with a standard shampoo and then dried.

were dyed in the following shades:

| Examples | Shades obtained |
|---|---|
| 1 | Bright red |
| 2 | Bright orange |
| 3 | Bright purple |

What is claimed is:

1. A ready-to-use composition for dyeing fibers, comprising:
   (i) at least one cationic direct dye chosen from compounds of formulae (I), (II), (III), (III') and (IV) below, and
   (ii) at least one thickening polymer;
   (a) wherein said compounds of formula (I) are chosen from compounds of formula:

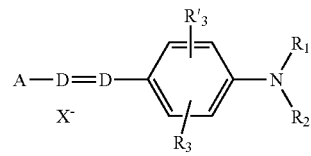

in which:
D is chosen from a nitrogen atom and a —CH group,
$R_1$ and $R_2$, which may be identical or different, are chosen from a hydrogen atom; a 4'-aminophenyl radical; and $C_1$-$C_4$ alkyl radicals which can optionally be substituted with a radical chosen from —CN, —OH and —NH$_2$ radicals or form, with each other or a carbon atom of the benzene ring of formula (I), a heterocycle optionally containing a heteroatom chosen from oxygen and nitrogen, which can be substituted with at least one radical chosen from $C_1$-$C_4$ alkyl radicals;
$R_3$ and $R'_3$, which may be identical or different, are chosen from a hydrogen atom, halogen atoms, a cyano radical, $C_1$-$C_4$ alkyl radicals, $C_1$-$C_4$ alkoxy radicals and acetyloxy radicals,
$X^-$ is chosen from anions,
A is chosen from structures $A_1$ to $A_{17}$ and $A_{19}$ below:

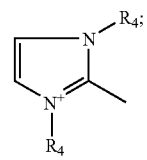

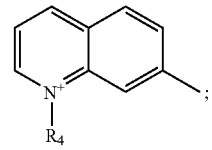

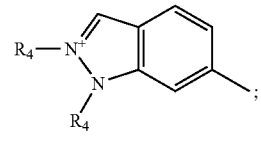

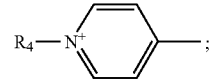

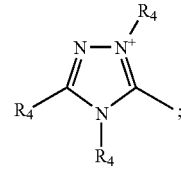

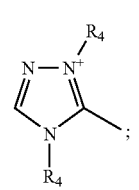

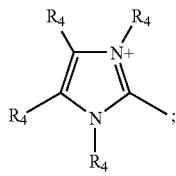
A7

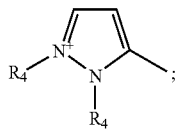
A8

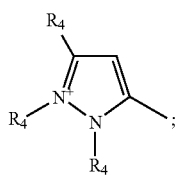
A9

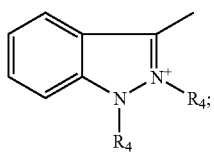
A10

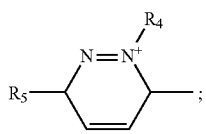
A11

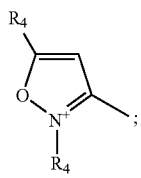
A12

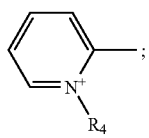
A13

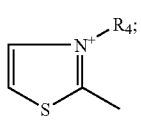
A14

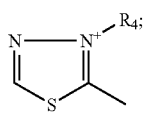
A15

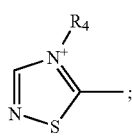
A16

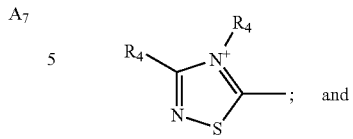
A17 and

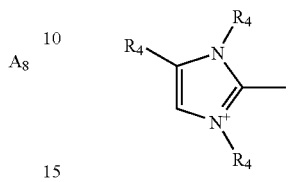
A19 in which:

$R_4$ is chosen from $C_1$-$C_4$ alkyl radicals which can be substituted with a hydroxyl radical, and $R_5$ is chosen from $C_1$-$C_4$ alkoxy radicals, and wherein when D represents —CH, when A represents $A_4$ or $A_{13}$ and when $R_3$ is not an alkoxy radical, $R_1$ and $R_2$ are not both a hydrogen atom;

(b) wherein said compounds of formula (II) are chosen from compounds of formula:

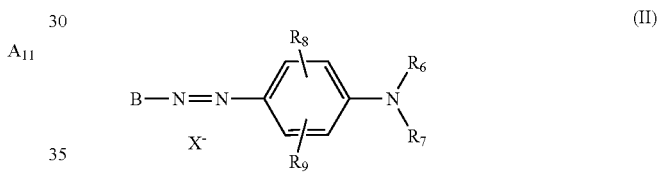

(II)

in which:

$R_6$ is chosen from a hydrogen atom and $C_1$-$C_4$ alkyl radicals, $R_7$ is chosen from a hydrogen atom, alkyl radicals which can be substituted with a species chosen from a —CN radical and an amino group, and a 4'-aminophenyl radical, or forms, with $R_6$, a heterocycle optionally comprising at least one heteroatom chosen from oxygen and nitrogen, which can be substituted with $C_1$-$C_4$ alkyl radicals, $R_8$ and $R_9$, which may be identical or different, are chosen from a hydrogen atom, halogen atoms, $C_1$-$C_4$ alkyl radicals, $C_1$-$C_4$ alkoxy radicals and a —CN radical, $X^-$ is chosen from anions, B is chosen from structures $B_1$ to $B_6$ below:

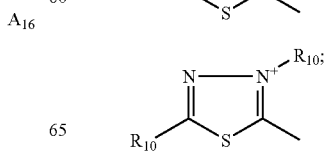
B1

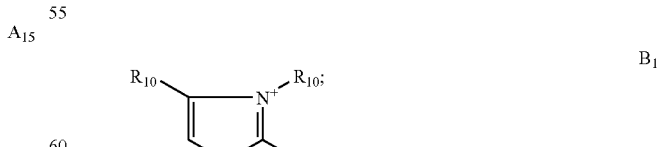
B2

-continued

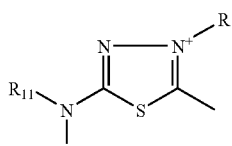 B3

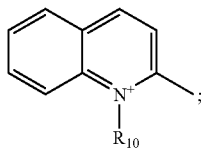 B4

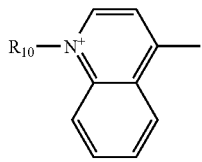 B5 and

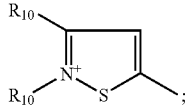 B6 in which:
R$_{10}$ is chosen from C$_1$-C$_4$ alkyl radicals, and
R$_{11}$ and R$_{12}$, which may be identical or different, are chosen from a hydrogen atom and C$_1$-C$_4$ alkyl radicals;
(c) wherein said compounds of formulae (III) and (III') are chosen from compounds of formulae:

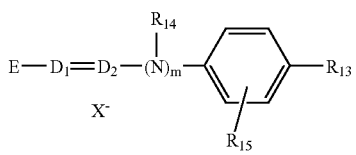 (III)

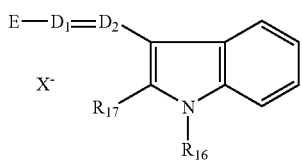 (III')

in which:
R$_{13}$ is chosen from a hydrogen atom, C$_1$-C$_4$ alkoxy radicals, halogen atoms and an amino radical,
R$_{14}$ is chosen from a hydrogen atom, C$_1$-C$_4$ alkyl radicals or forms, with a carbon atom of the benzene ring, a heterocycle optionally containing an oxygen heteroatom and/or substituted with at least one radical chosen from C$_1$-C$_4$ alkyl radicals,
R$_{15}$ is chosen from a hydrogen atom and halogen atoms,
R$_{16}$ and R$_{17}$, which may be identical or different, are chosen from a hydrogen atom and C$_1$-C$_4$ alkyl radicals,
D$_1$ and D$_2$, which may be identical or different, are chosen from a nitrogen atom and a —CH group,
m=0 or 1,
wherein when R$_{13}$ is an unsubstituted amino group, D$_1$ and D$_2$ are both a —CH group and m=0,
X$^-$ is chosen from anions, E is chosen from structures E$_1$ to E$_8$ below:

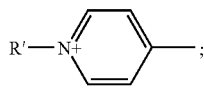 E1

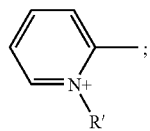 E2

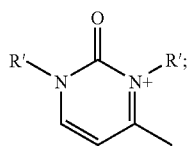 E3

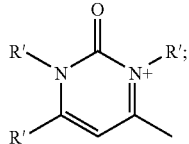 E4

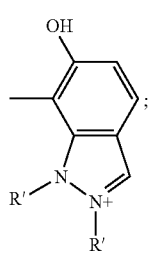 E5

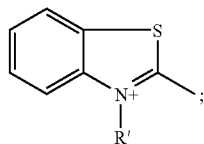 E6

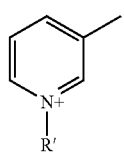 E7

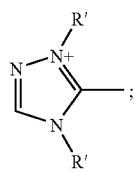 E8 in which R' is chosen from C$_1$-C$_4$ alkyl radicals;
wherein when m=0 and when D$_1$ represents a nitrogen atom, E can be further chosen from structure E$_9$ below:

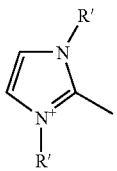

in which R' is chosen from $C_1$-$C_4$ alkyl radicals;
(d) wherein said compounds of formula (IV) are chosen from compounds of formula:

 (IV)

in which:
G is chosen from structures $G_1$ to $G_3$ below:

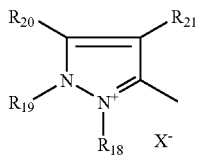 $G_1$

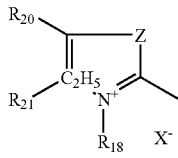 $G_2$

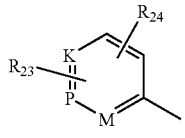 $G_3$ in which:
- $R_{18}$ is chosen from $C_1$-$C_4$ alkyl radicals and a phenyl radical which can optionally be substituted with $C_1$-$C_4$ alkyl radicals or a halogen atom chosen from chlorine, bromine, iodine and fluorine;
- $R_{19}$ is chosen from $C_1$-$C_4$ radicals and a phenyl radical;
- $R_{20}$ and $R_{21}$, which may be identical or different, are chosen from $C_1$-$C_4$ alkyl radicals and a phenyl radical, or
- together form, in $G_1$, a benzene ring substituted with at least one radical chosen from $C_1$-$C_4$ alkyl radicals, $C_1$-$C_4$ alkoxy radicals and $NO_2$ radicals, or
- together form, in $G_2$, a benzene ring optionally substituted with at least one radical chosen from $C_1$-$C_4$ alkyl radicals, $C_1$-$C_4$ alkoxy radicals and $NO_2$ radicals;
- $R_{20}$ can be further chosen from a hydrogen atom;
- Z is chosen from an oxygen atom, a sulphur atom and —$NR_{19}$ radicals;
- M is chosen from a —CH radical, —C($C_1$-$C_4$ alkyl) radicals and —$N^+R_{22}(X^-)_r$ radicals;
- K is chosen from a —CH radical, —C($C_1$-$C_4$ alkyl) radicals and —$N^+R_{22}(X^-)_r$ radicals;
- P is chosen from a —CH radical, —C($C_1$-$C_4$ alkyl) radicals and —$N^+R_{22}(X^-)_r$ radicals;

wherein r denotes zero or 1;
wherein $R_{22}$ is chosen from an $O^-$ anion, $C_1$-$C_4$ alkoxy radicals, and $C_1$-$C_4$ alkyl radicals;
$R_{23}$ and $R_{24}$, which may be identical or different, are chosen from a hydrogen atom, halogen atoms chosen from chlorine, bromine, iodine and fluorine, $C_1$-$C_4$ alkyl radicals, $C_1$-$C_4$ alkoxy radicals and an —$NO_2$ radical;
$X^-$ is chosen from anions;
wherein if $R_{22}$ is $O^-$, r is zero;
wherein if K or P or M is $C_1$-$C_4$—$N^+$-alkyl $X^-$, either $R_{23}$ or $R_{24}$ is not a hydrogen atom;
wherein if K is —$N^+R_{22}(X^-)_r$, M and P are the same and are chosen from a —CH radical and —C($C_1$-$C_4$ alkyl) radicals;
wherein if M denotes —$N^+R_{22}(X^-)_r$, K and P are the same and are chosen from a —CH radical and —C($C_1$-$C_4$ alkyl) radicals;
if P is —$N^+R_{22}(X^-)_r$, K and M are the same and are chosen from a —CH radical and —C($C_1$-$C_4$ alkyl) radicals;
if Z is a sulphur atom with $R_{21}$ being a radical chosen from $C_1$-$C_4$ alkyl radicals, $R_{20}$ is not a hydrogen atom;
if Z is —$NR_{22}$ with $R_{19}$ being a radical chosen from $C_1$-$C_4$ alkyl radicals, at least one of the radicals $R_{18}$, $R_{20}$ and $R_{21}$ of $G_2$ is not chosen from $C_1$-$C_4$ alkyl radicals;
J is chosen from:
(1) radicals chosen from structure $J_1$ below:

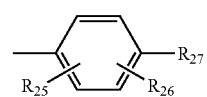 $J_1$ in which:
$R_{25}$ is chosen from a hydrogen atom, halogen atoms chosen from chlorine, bromine, iodine and fluorine, $C_1$-$C_4$ alkyl radicals, $C_1$-$C_4$ alkoxy radicals, an —OH radical, an —$NO_2$ radical, —$NHR_{28}$ radicals, —$NR_{29}R_{30}$ radicals, —NHCO ($C_1$-$C_4$) alkyl radicals, or forms, with $R_{26}$, a 5- or 6-membered ring optionally containing at least one heteroatom chosen from nitrogen, oxygen and sulphur;
$R_{26}$ is chosen from a hydrogen atom, halogen atoms chosen from chlorine, bromine, iodine and fluorine, $C_1$-$C_4$ alkyl radicals, $C_1$-$C_4$ alkoxy radicals or forms, with $R_{27}$ or $R_{28}$, a 5- or 6-membered ring optionally containing at least one heteroatom chosen from nitrogen, oxygen and sulphur;
$R_{27}$ is chosen from a hydrogen atom, an —OH radical, —$NHR_{28}$ radicals and —$NR_{29}R_{30}$ radicals;
$R_{28}$ is chosen from a hydrogen atom, $C_1$-$C_4$ alkyl radicals, $C_1$-$C_4$ monohydroxyalkyl radicals, $C_2$-$C_4$ polyhydroxyalkyl radicals and a phenyl radical;
$R_{29}$ and $R_{30}$, which may be identical or different, are chosen from $C_1$-$C_4$ alkyl radicals, $C_1$-$C_4$ monohydroxyalkyl radicals and $C_2$-$C_4$ polyhydroxyalkyl radicals;
(2) 5- and 6-membered nitrogenous heterocyclic groups optionally containing other heteroatoms and/or carbonyl groups and optionally substituted with at least one radical chosen from $C_1$-$C_4$ alkyl radicals, an amino radical, a phenyl radical, and
wherein said at least one thickening polymer is chosen from polymers comprising:

(ii)$_1$—nonionic amphiphilic polymers, comprising: at least one hydrophilic unit and at least one unit comprising a fatty chain;

(ii)$_2$—anionic amphiphilic polymers, comprising: at least one hydrophilic unit and at least one unit comprising a fatty chain; and (iii)$_3$—cationic amphiphilic polymers, comprising at least one hydrophilic unit and at least one unit comprising a fatty chain.

2. The composition according to claim 1, wherein said fibers are human keratin fibers.

3. The composition according to claim 1, wherein said halogen atoms of $R_3$, $R'_3$, $R_8$, $R_9$, $R_{13}$ and $R_{15}$, which may be identical or different, are chosen from chlorine, bromine, iodine and fluorine.

4. The composition according to claim 1, wherein said anions are chosen from chloride, methyl sulphate, acetate and perchlorate.

5. The composition according to claim 1, wherein said at least one cationic direct dye chosen from compounds of formula (I) is chosen from compounds of formulae (I1) to (I54) below:

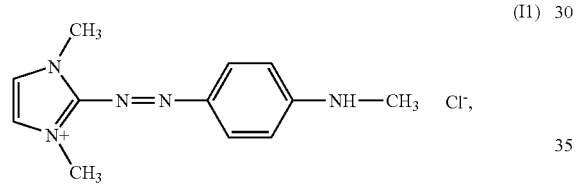
(I1)

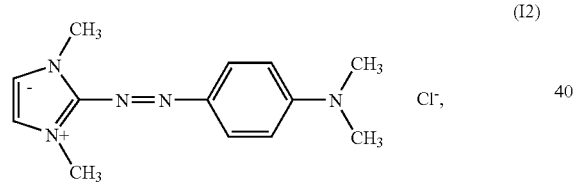
(I2)

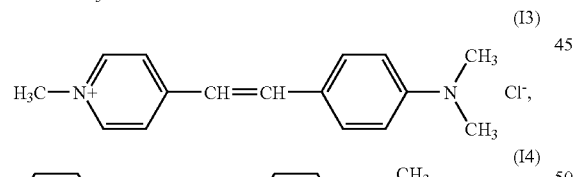
(I3)

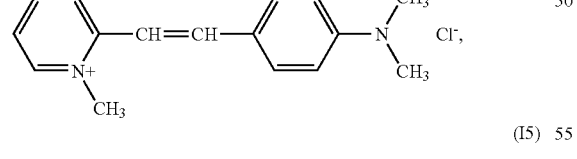
(I4)

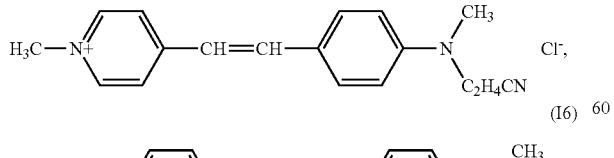
(I5)

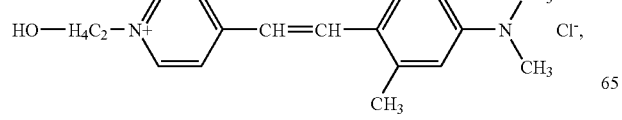
(I6)

-continued

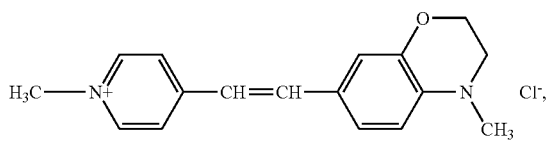
(I7)

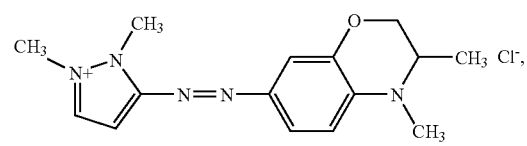
(I8)

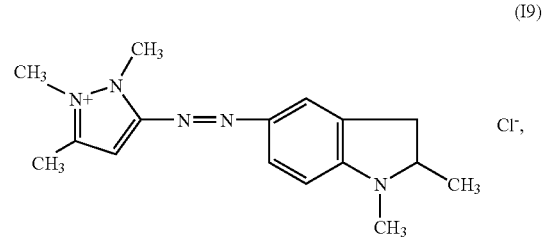
(I9)

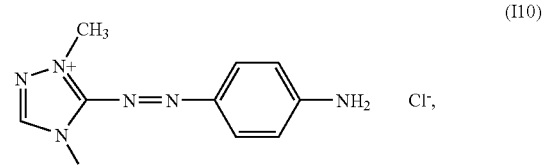
(I10)

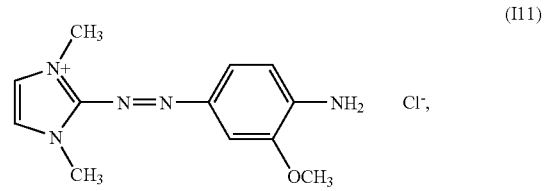
(I11)

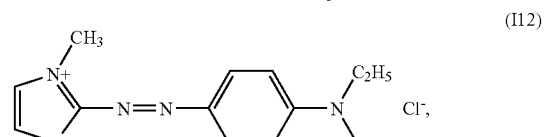
(I12)

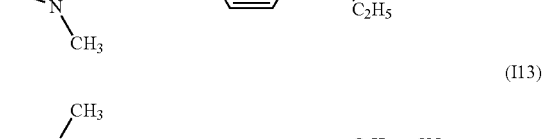
(I13)

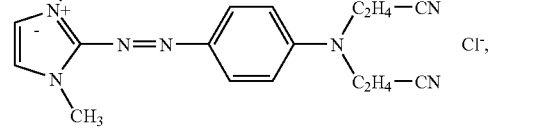
(I14)

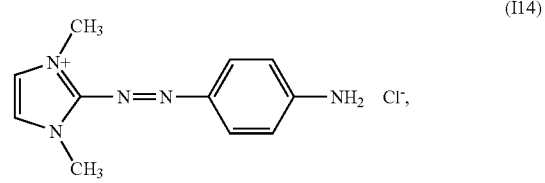

-continued
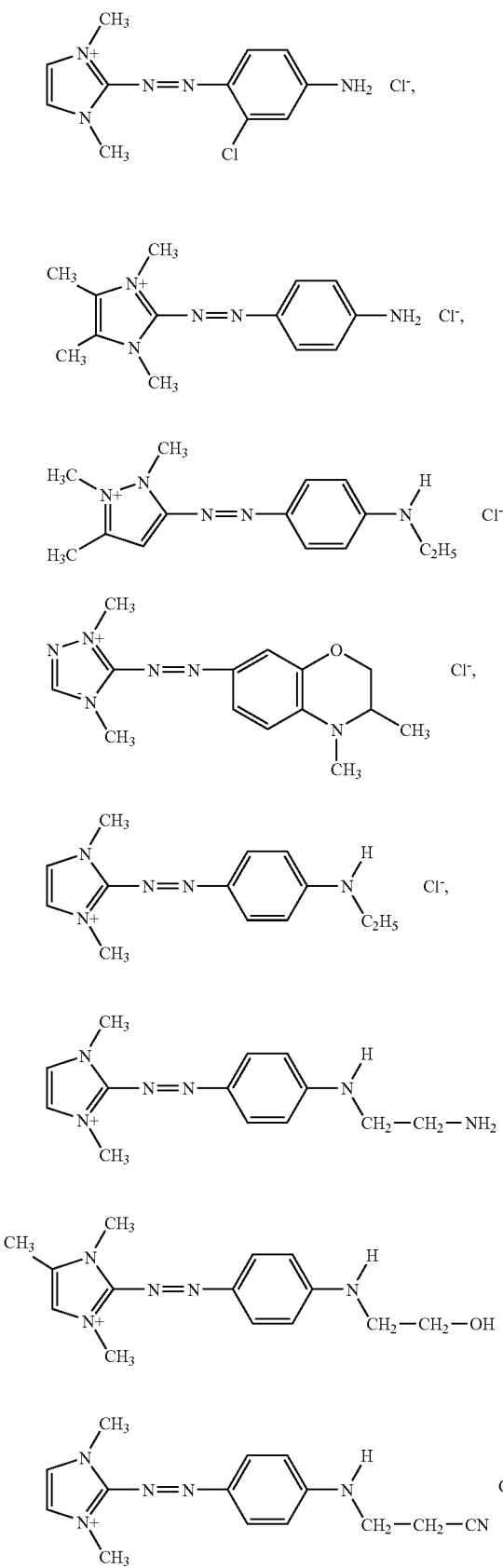
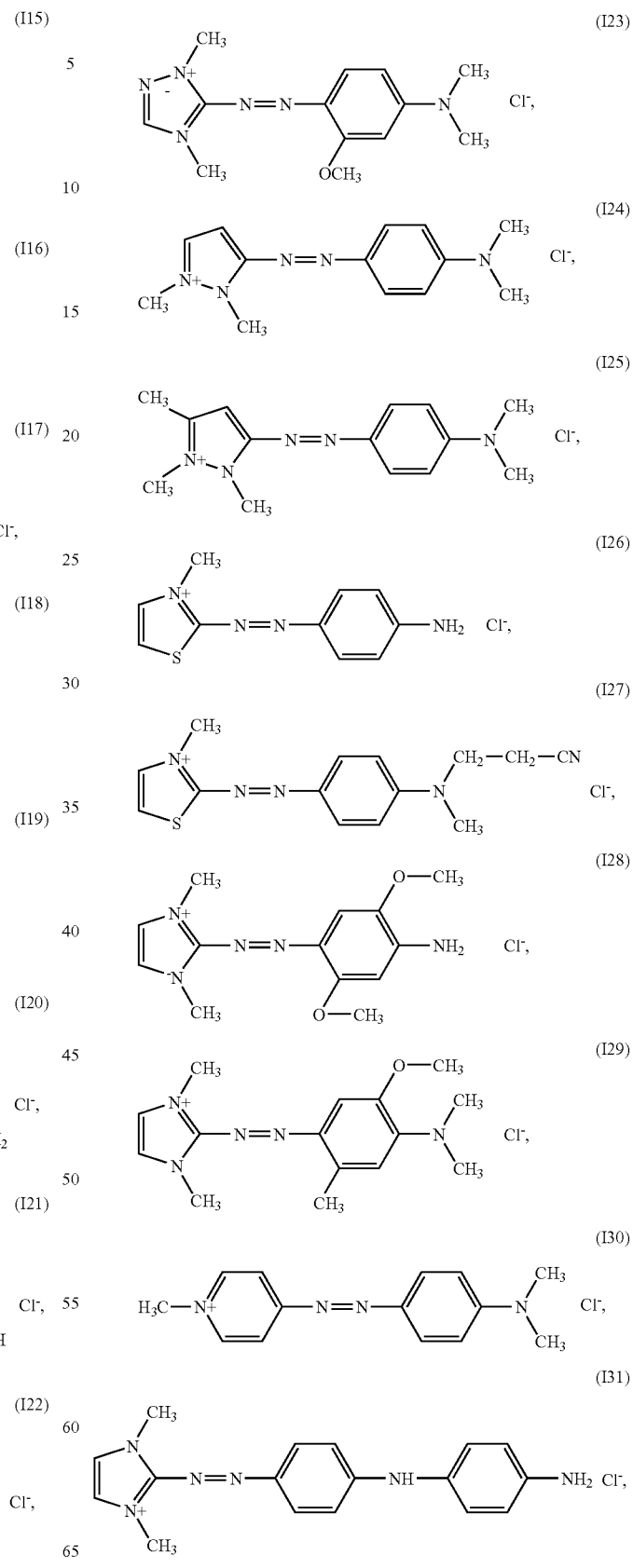

-continued
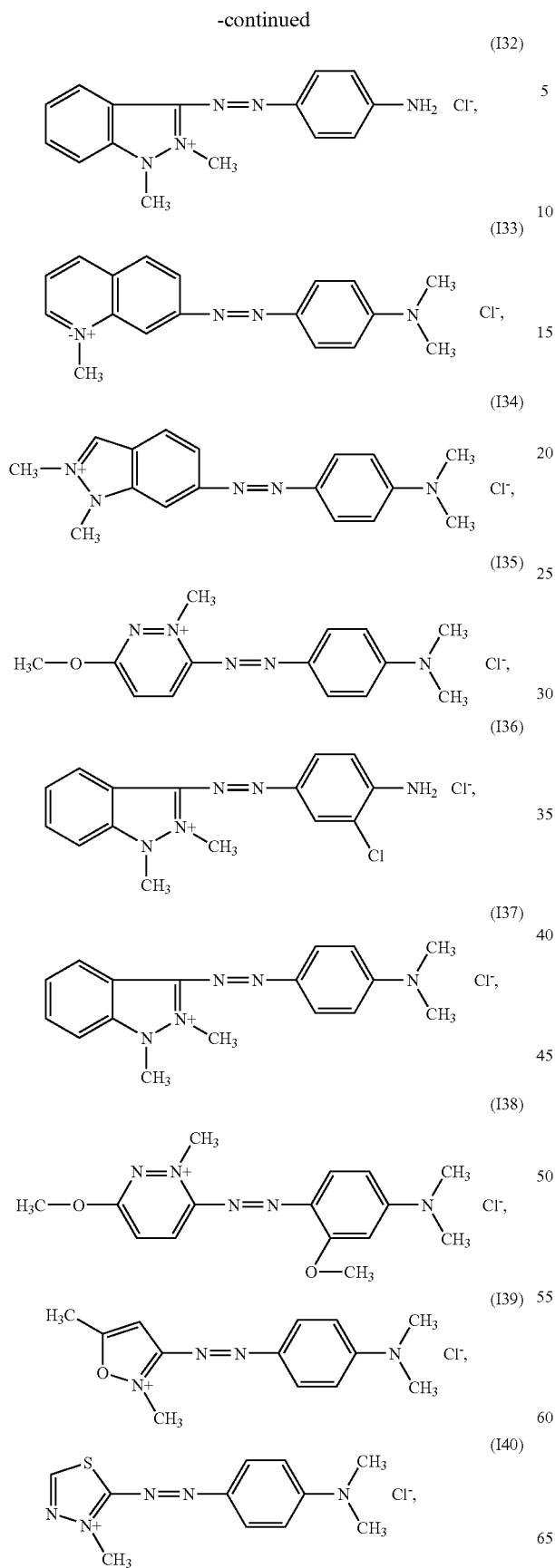
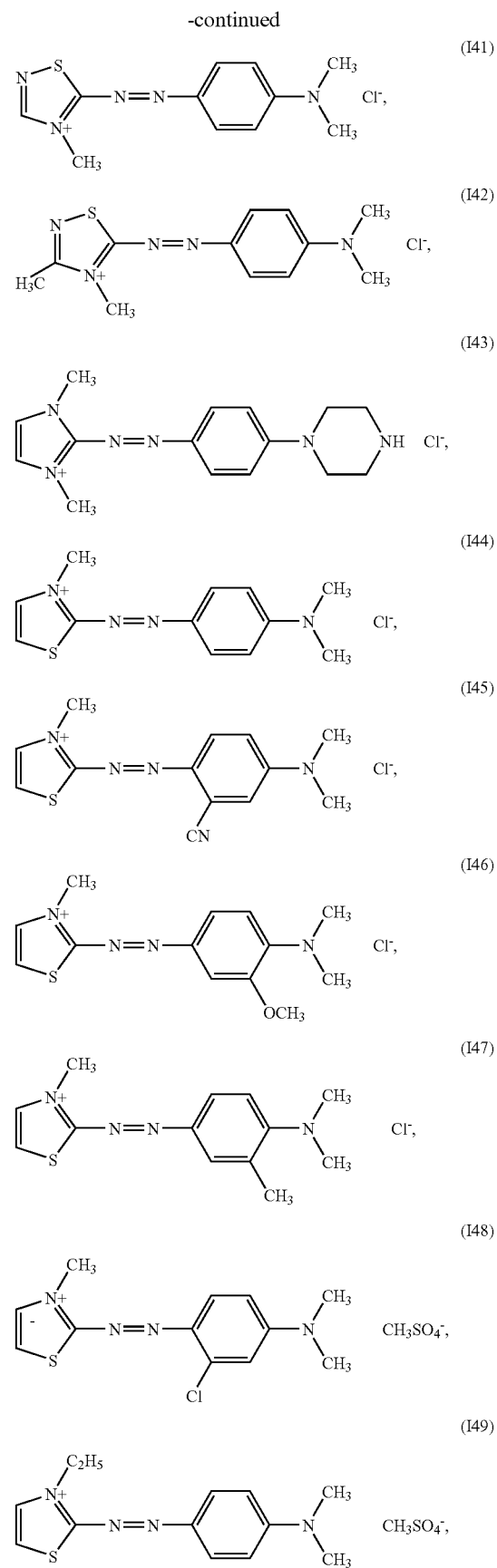

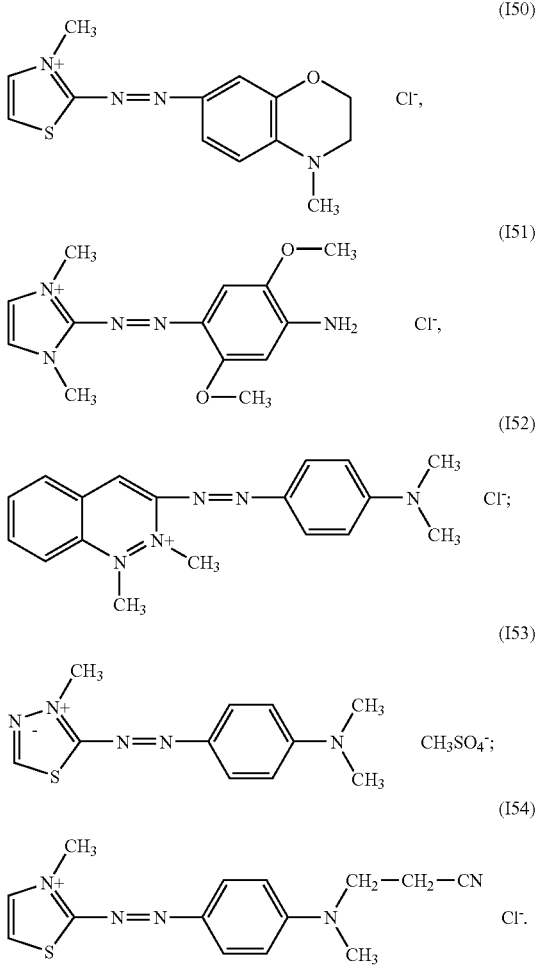

6. The composition according to claim 5, wherein said at least one cationic direct dye chosen from compounds of formula (I) is chosen from said compounds of formulae (I1), (I2), (I14) and (I31).

7. The composition according to claim 1, wherein said at least one cationic direct dye is present in an amount ranging from 0.001 to 10% by weight relative to the total weight of the composition.

8. The composition according to claim 7, wherein said at least one cationic direct dye is present in an amount ranging from 0.005 to 5% by weight relative to the total weight of the composition.

9. The composition according to claim 1, wherein said at least one thickening polymer is chosen from nonionic amphiphilic polymers, and said at least one hydrophilic unit is chosen from celluloses modified with at least one unit comprising a fatty chain.

10. The composition according to claim 9, wherein said celluloses are chosen from hydroxyethylcelluloses, and wherein said at least one unit is comprising a fatty chain is chosen from alkyl, aralkyl, and alkylaryl groups and mixtures thereof.

11. The composition according to claim 10, wherein said at least one unit comprising a fatty chain is chosen from $C_8$-$C_{22}$ chains.

12. The composition according to claim 10, wherein said at least one unit comprising a fatty chain is chosen from $C_{16}$ alkyl groups.

13. The composition according to claim 9, wherein said at least unit comprising a fatty chain is chosen from polyalkylene glycol alkylphenyl ethers.

14. The composition according to claim 13, wherein said polyalkylene glycol alkylphenyl ethers are polyethylene glycol (15) nonylphenyl ether.

15. The composition according to claim 1, wherein said at least one thickening polymer is chosen from nonionic amphiphilic polymers, and further wherein said at least one hydrophilic unit is chosen from hydroxypropylguars modified with at least one unit comprising a fatty chain.

16. The composition according to claim 15, wherein said at least one unit comprising a fatty chain is chosen from $C_{14}$, $C_{20}$ and $C_{22}$ alkyl chains.

17. The composition according to claim 1, wherein said at least one thickening polymer is chosen from nonionic amphiphilic polymers, and further wherein said at least one hydrophilic unit is chosen from polyurethane ethers comprising at least one unit comprising a fatty chain chosen from $C_8$-$C_{30}$ alkyl and alkenyl chains.

18. The composition according to claim 1, wherein said at least one thickening polymer chosen from nonionic amphiphilic polymers is chosen from copolymers of vinylpyrrolidone and of hydrophobic monomers containing a fatty chain.

19. The composition according to claim 18, wherein said copolymers are chosen from vinylpyrrolidone/hexadecene copolymers and vinylpyrrolidone/eicosene copolymers.

20. The composition according to claim 1, wherein said at least one thickening polymer chosen from nonionic amphiphilic polymers is chosen from copolymers of $C_1$-$C_6$ alkyl methacrylates and of $C_1$-$C_6$ alkyl acrylates and of amphiphilic monomers comprising at least one fatty chain.

21. The composition according to claim 20, wherein said thickening polymer chosen from nonionic amphiphilic polymers is chosen from oxyethylated methyl methacrylate/stearyl acrylate copolymers.

22. The composition according to claim 1, wherein said at least one thickening polymer chosen from nonionic amphiphilic polymers is chosen from copolymers of hydrophilic methacrylates and of hydrophilic acrylates and of hydrophobic monomers comprising at least one fatty chain.

23. The composition according to claim 22, wherein said at least one thickening polymer chosen from nonionic amphiphilic polymers is chosen from polyethylene glycol methacrylate/lauryl methacrylate copolymers.

24. The composition according to claim 1, wherein said at least one thickening polymer chosen from nonionic amphiphilic polymers is chosen from: cetyl hydroxyethylecellulose, copolymers of vinylpyrrolidone/hexadecene, vinylpyrrolidone/eicosene, copolymers of oxyethylated methyl methacrylate/stearyl acrylate, and polyethylene glycol methacrylate/lauryl methacrylate.

25. The composition according to claim 1, wherein said least one thickening polymer is present in an amount ranging from 0.01 to 10% by weight relative to the total weight of said composition.

26. The composition according to claim 25, wherein said at least one thickening polymer is present in an amount ranging from 0.1 to 5% by weight relative to the total weight of said composition.

27. The composition according to claim 1, further comprising water or a mixture of water and at least one organic solvent.

28. The composition according to claim 1, wherein said composition has a pH ranging from 2 to 11.

29. The composition according to claim 28, wherein said composition has a pH ranging from 5 to 10.

30. The composition according to claim 1, further comprising at least one non-cationic direct dye chosen from nitrobenzene dyes, anthraquinone dyes, naphthoquinone dyes, triarylmethane dyes, xanthene dyes and azo dyes.

31. The composition according to claim 1, further comprising at least one oxidation base chosen from para-phenylenediamines, bis(phenyl) alkylenediamines, para-aminophenols, ortho-aminophenols and heterocyclic bases.

32. The composition according to claim 31, wherein said at least one oxidation base is present in an amount ranging from 0.0005 to 12% by weight relative to the total weight of said composition.

33. The composition according to claim 32, wherein said at least one oxidation base is present in an amount ranging from 0.005 to 6% by weight relative to the total weight of said composition.

34. The composition according to claim 31, further comprising at least one coupler chosen from meta-phenylenediamines, meta-aminophenols, meta-diphenols and heterocyclic couplers.

35. The composition according to claim 34, wherein said at least one coupler is present in amount ranging from 0.0001 to 10% by weight relative to the total weight of said composition.

36. The composition according to claim 34, wherein said at least one coupler is present in an amount ranging from 0.005 to 5% by weight relative to the total weight of said composition.

37. The composition according to claim 31, further comprising at least one oxidizing agent.

38. The composition according to claim 37, wherein said at least one oxidizing agent is chosen from hydrogen peroxide, urea peroxide, alkali metal bromates, persalts, and enzymes.

39. The composition according to claim 1, further comprising at least one oxidizing agent.

40. The composition according to claim 39, wherein said at least one oxidizing agent is chosen from hydrogen peroxide, urea peroxide, alkali metal bromates, persalts, and enzymes.

41. The composition according to claim 1, wherein said composition is in a form chosen from a shampoo, a cream, and a gel.

42. A ready-to-use composition for dyeing fibers, comprising:
  at least one thickening polymer chosen from polymers comprising:
    nonionic amphiphilic polymers, comprising: at least one hydrophilic unit and at least one unit comprising a fatty chain;
    anionic amphiphilic polymers, comprising: at least one hydrophilic unit and at least one unit comprising a fatty chain; and
    cationic amphiphilic polymers, comprising at least one hydrophilic unit and at least one unit comprising a fatty chain, and
  at least one cationic direct dye chosen from:

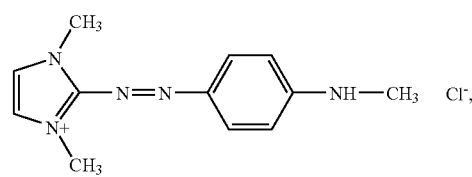

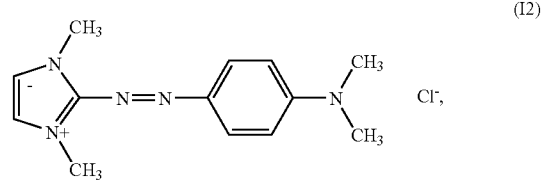

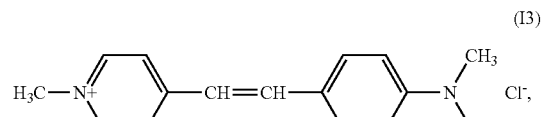

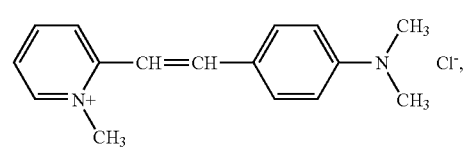

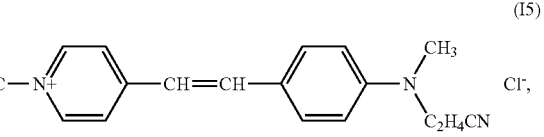

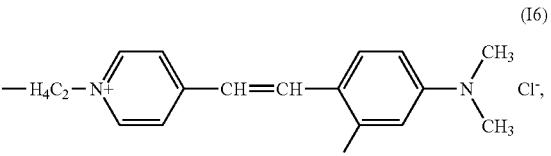

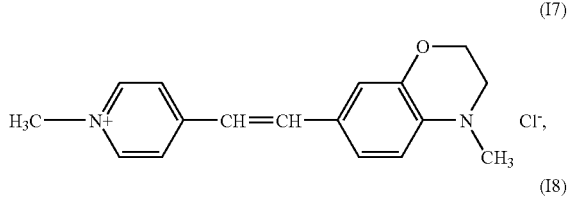

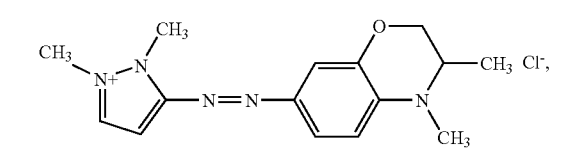

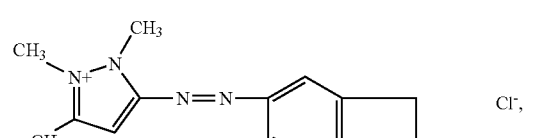

-continued (I10), (I11), (I12), (I13), (I14), (I15), (I16), (I17), (I18), (I19), (I20), (I21), (I22), (I23), (I24), (I25)

-continued

-continued
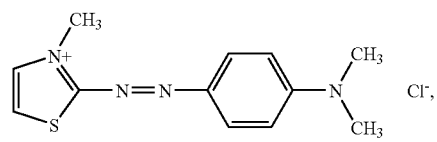 (I44)
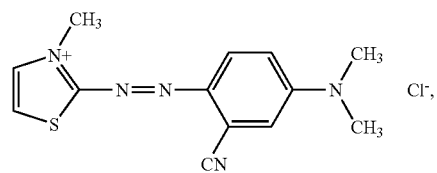 (I45)
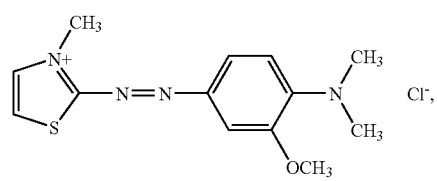 (I46)
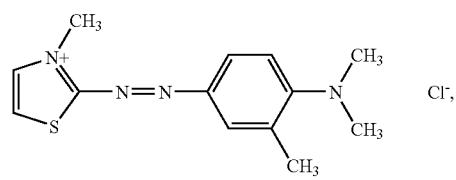 (I47)
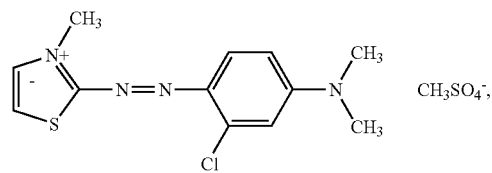 (I48)
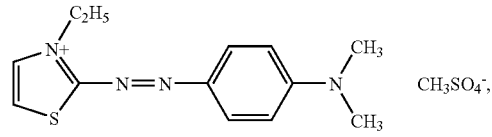 (I49)
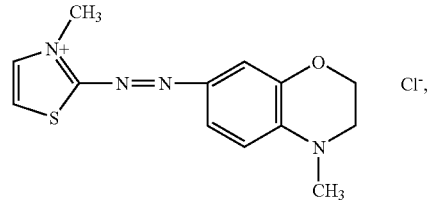 (I50)
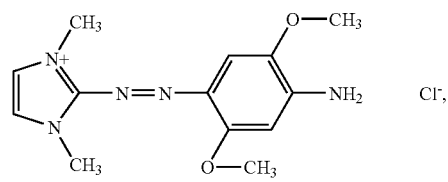 (I51)
-continued
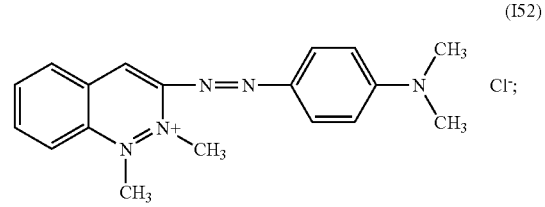 (I52)
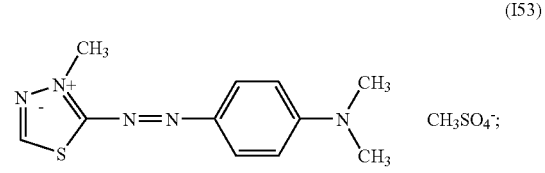 (I53)
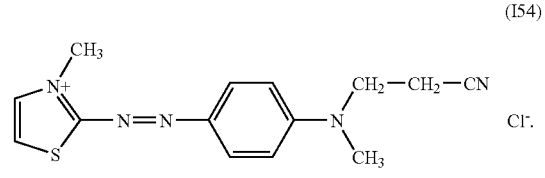 (I54)
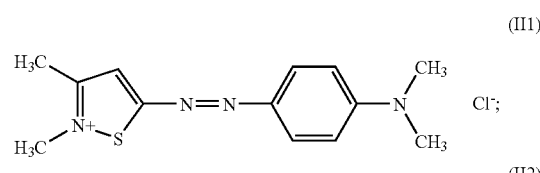 (II1)
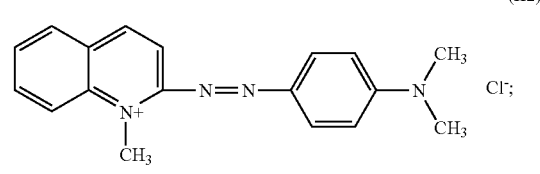 (II2)
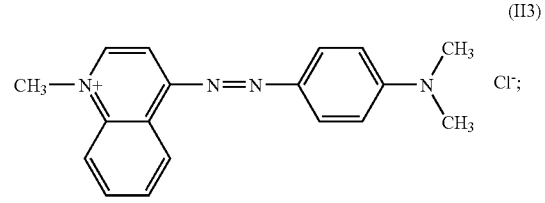 (II3)
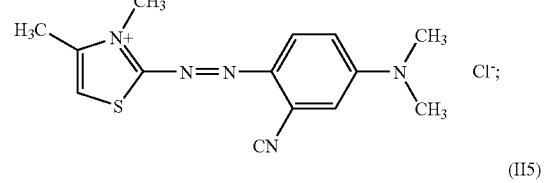 (II4)
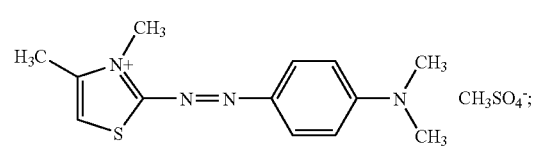 (II5)

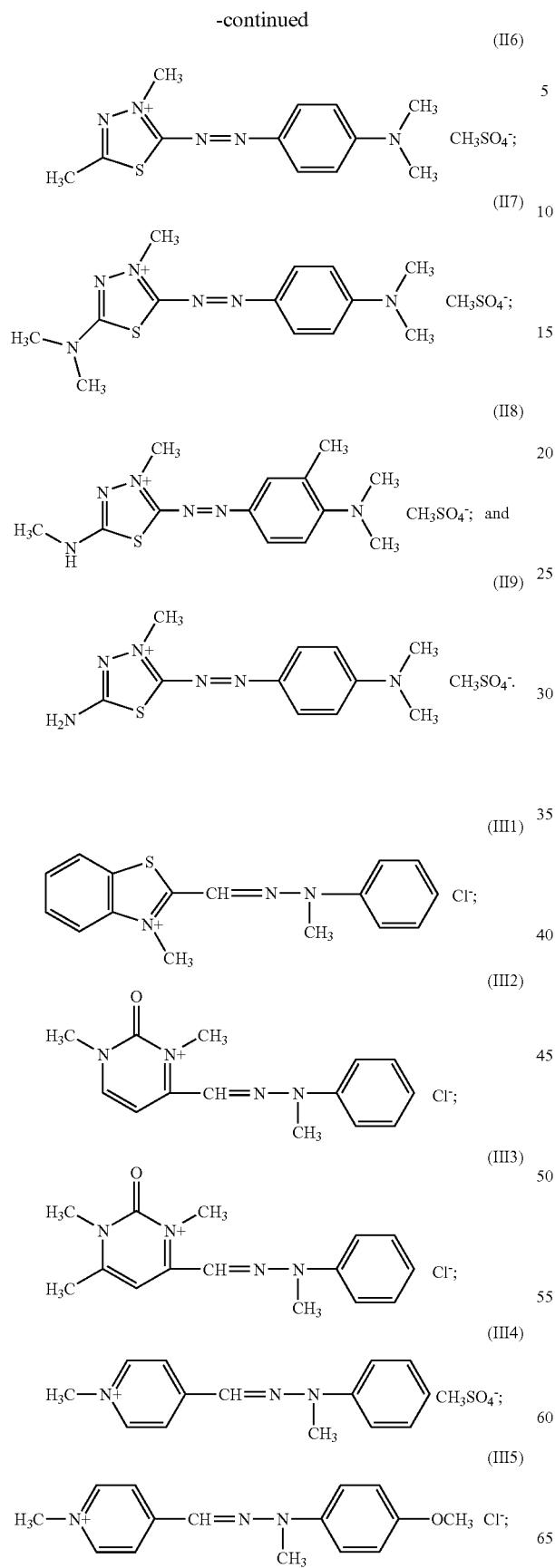
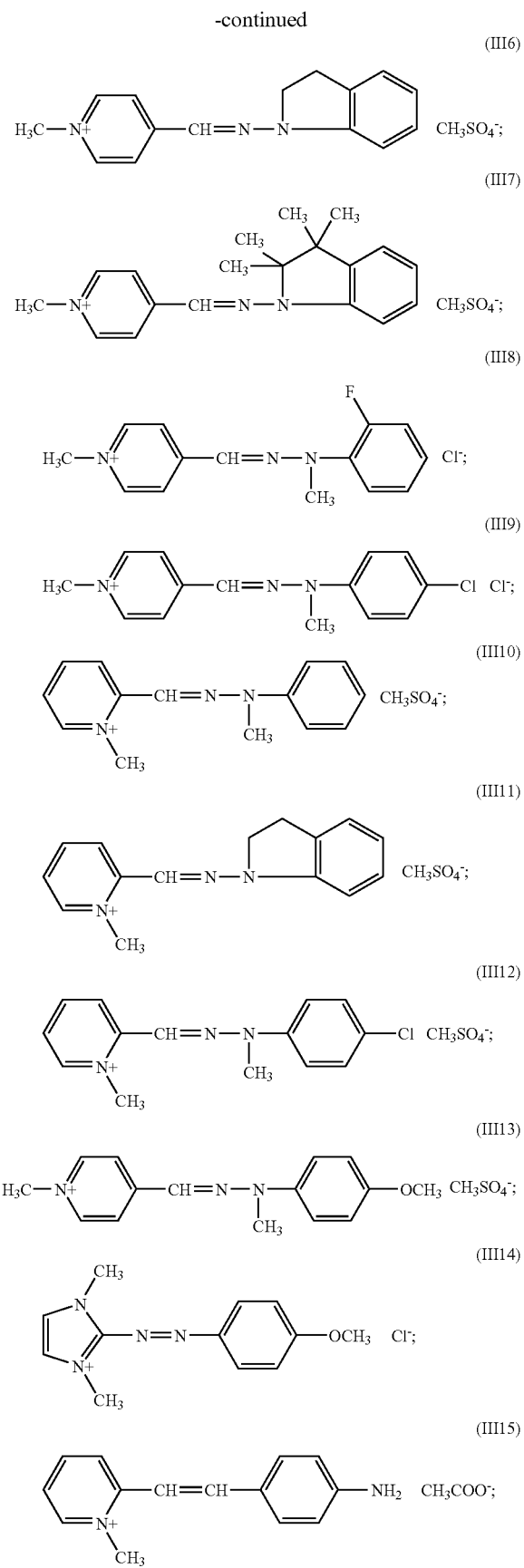

-continued
(III16)
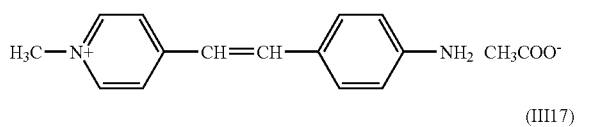
(III17)
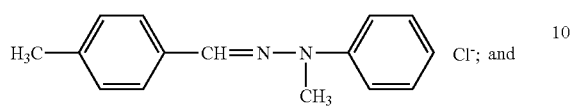
(III18)
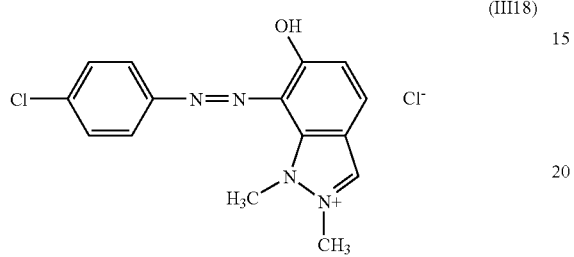
(III'1)
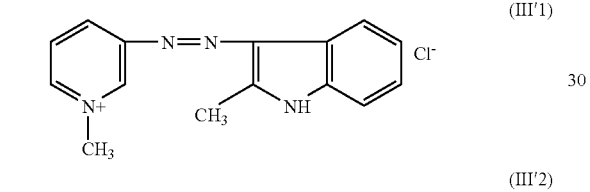
(III'2)
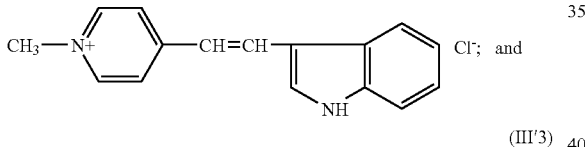
(III'3)
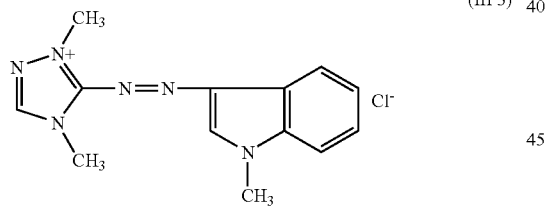
(IV)$_1$
(IV)$_2$
-continued
(IV)$_3$
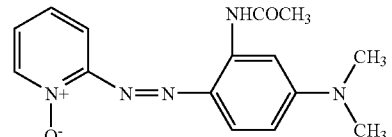
(IV)$_4$
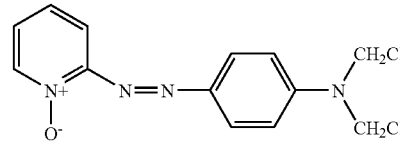
(IV)$_5$
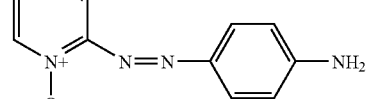
(IV)$_6$
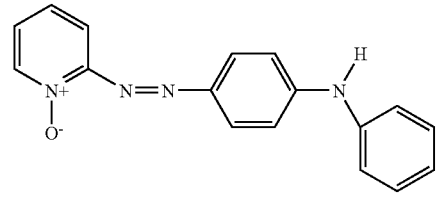
(IV)$_7$
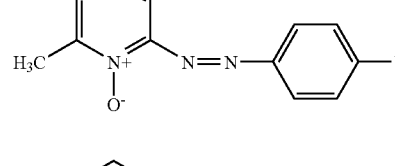
(IV)$_8$
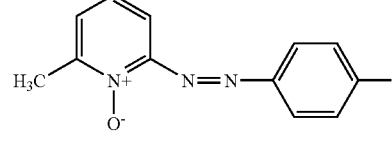
(IV)$_9$
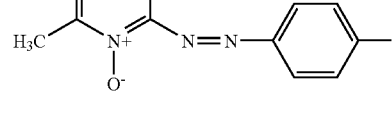
(IV)$_{10}$
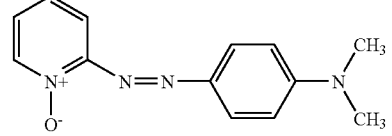

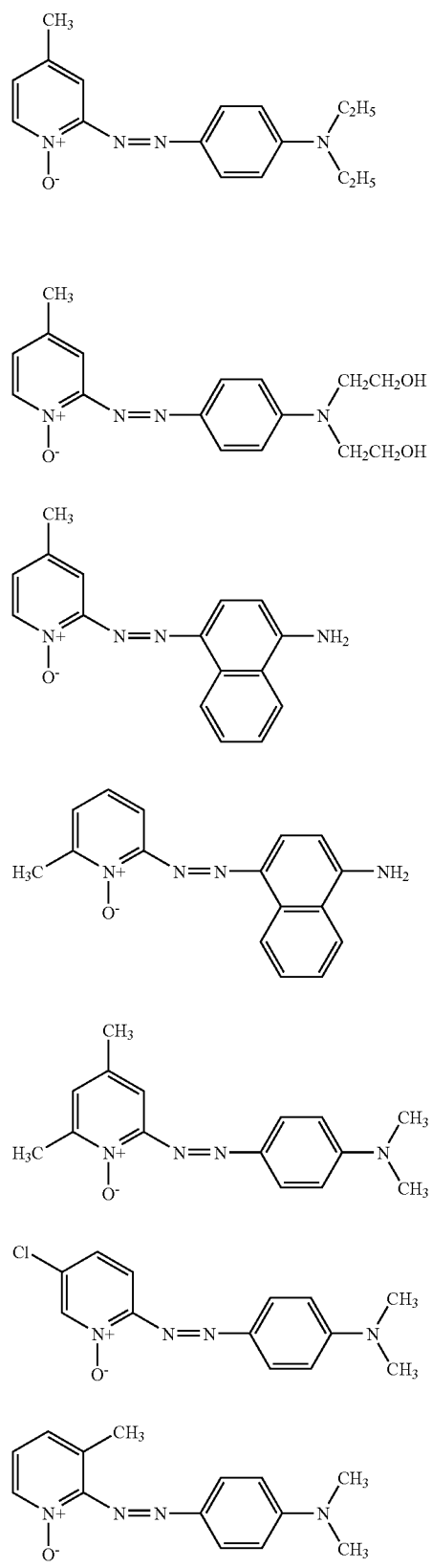
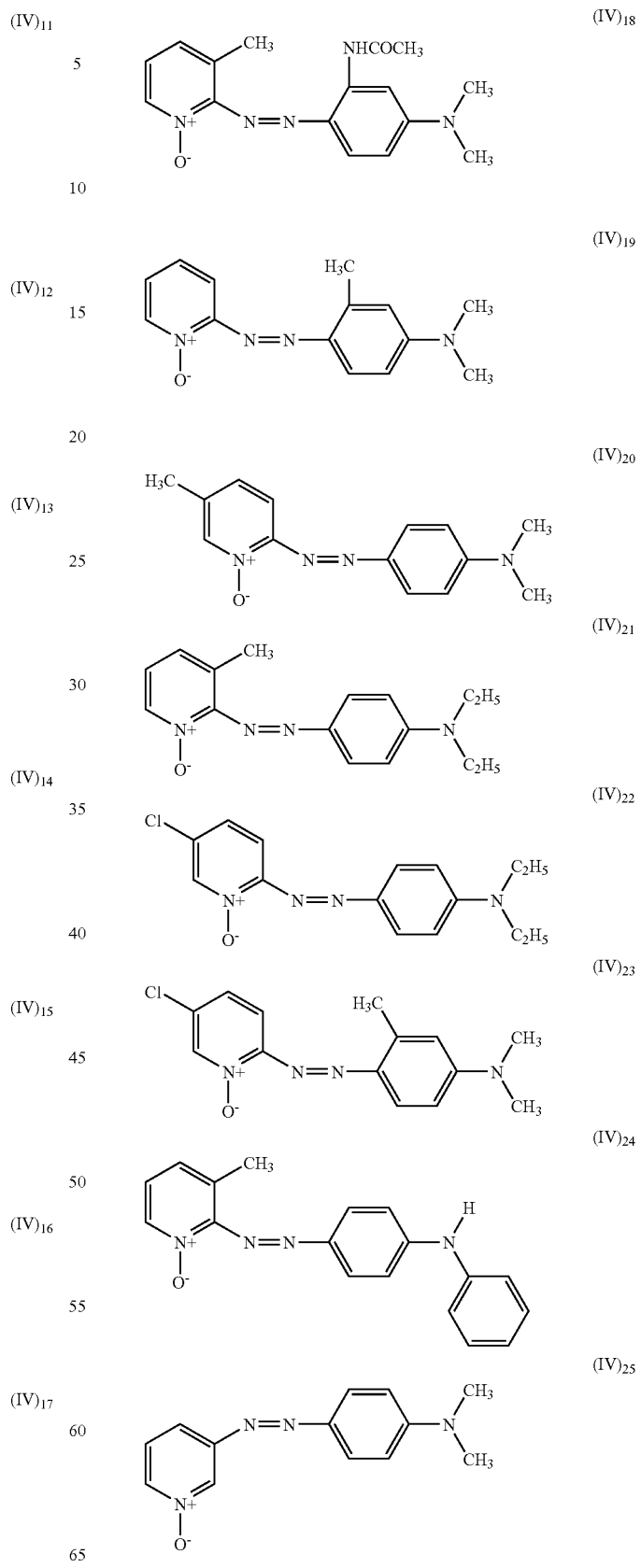

-continued
(IV)26
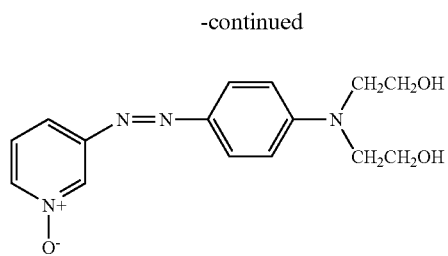
(IV)27
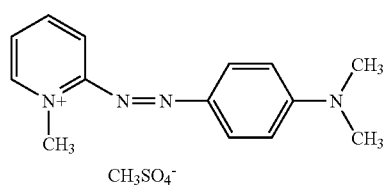
(IV)28
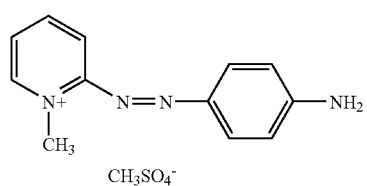
(IV)29
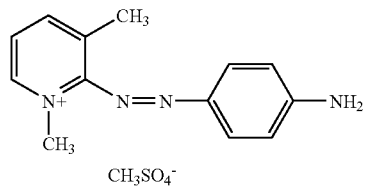
(IV)30
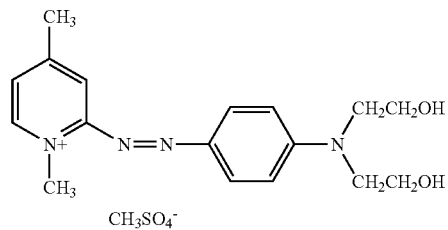
(IV)31
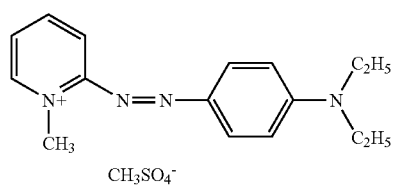
(IV)32
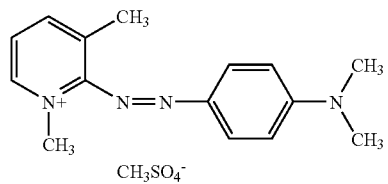
-continued
(IV)33
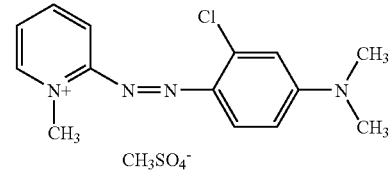
(IV)34
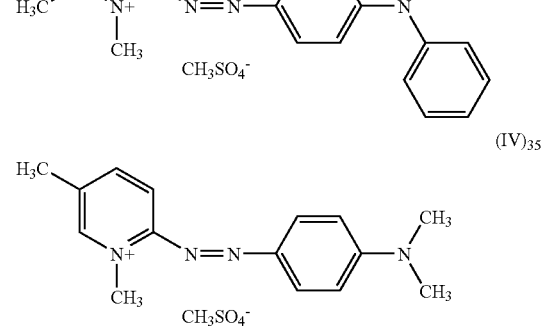
(IV)35
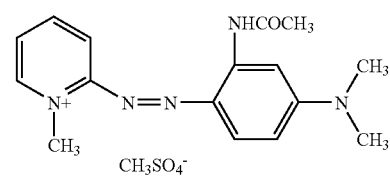
(IV)36
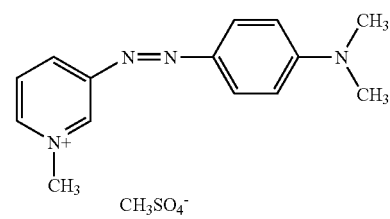
(IV)37
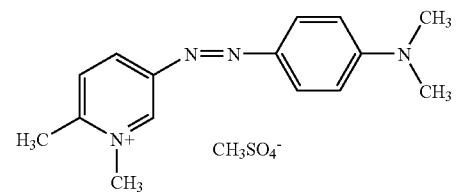
(IV)38
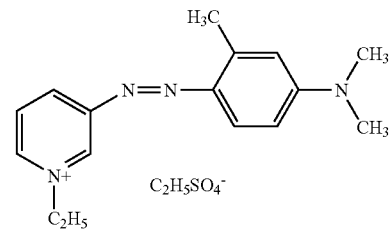
(IV)39

-continued
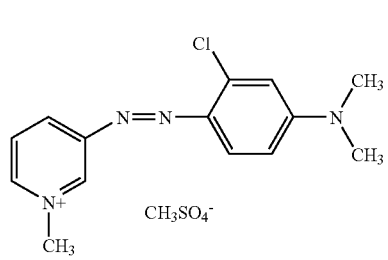
(IV)₄₀
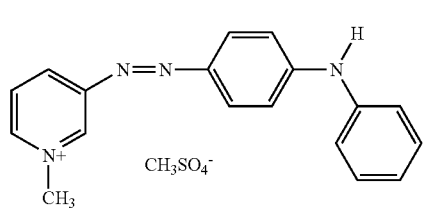
(IV)₄₁
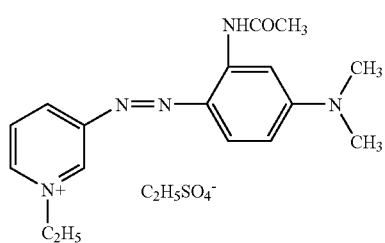
(IV)₄₂
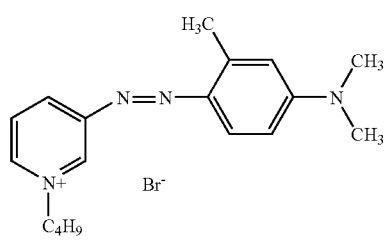
(IV)₄₃
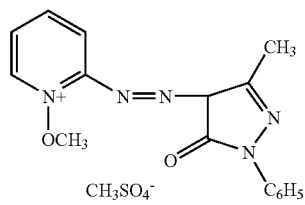
(IV)₄₄
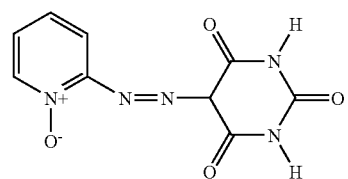
(IV)₄₅
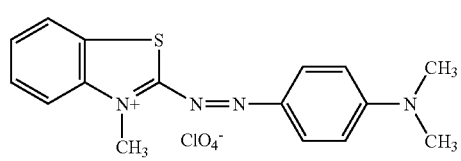
(IV)₄₆
-continued
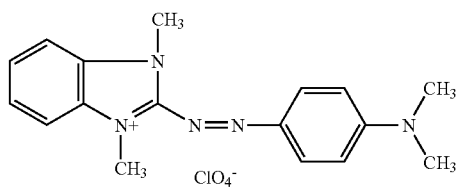
(IV)₄₇
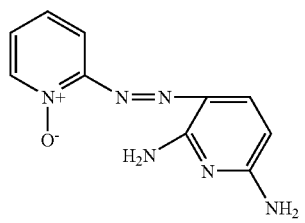
(IV)₄₈
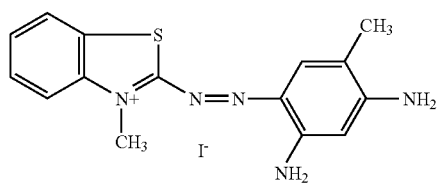
(IV)₄₉
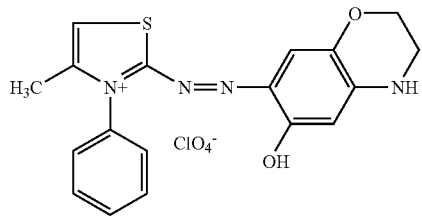
(IV)₅₀
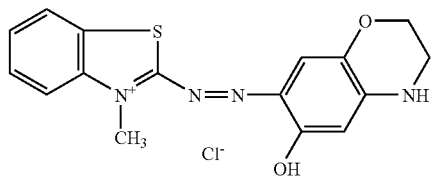
(IV)₅₁
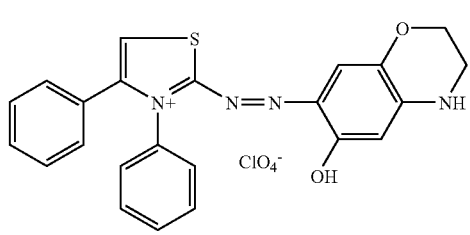
(IV)₅₂
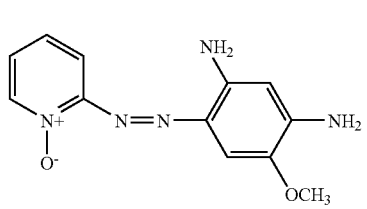
(IV)₅₃

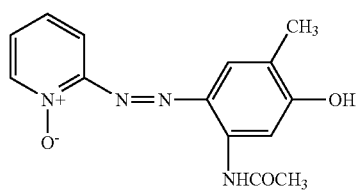 (IV)₅₄
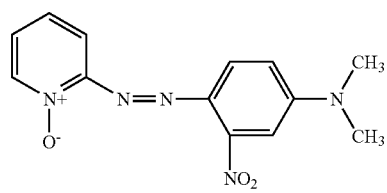 (IV)₆₁
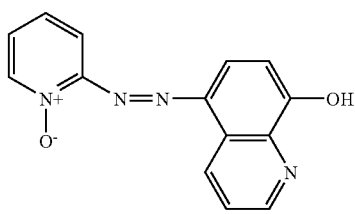 (IV)₅₅
(IV)₆₂
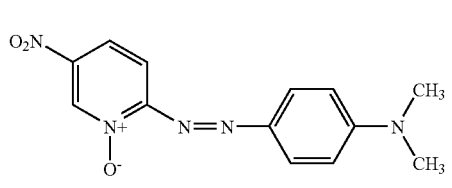
(IV)₅₆
(IV)₆₃
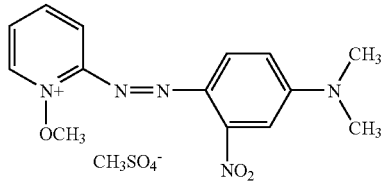
(IV)₅₇
(IV)₆₄
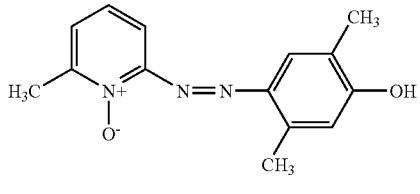
(IV)₅₈
(IV)₆₅
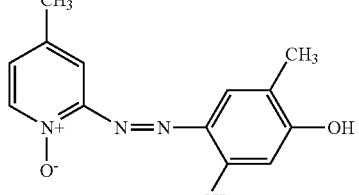
(IV)₅₉
(IV)₆₆
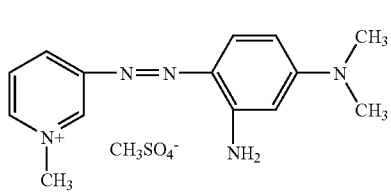
(IV)₆₀
(IV)₆₇

-continued (IV)₆₈
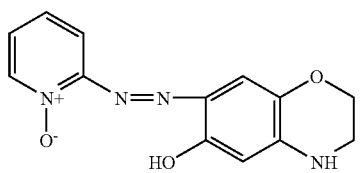

(IV)₆₉
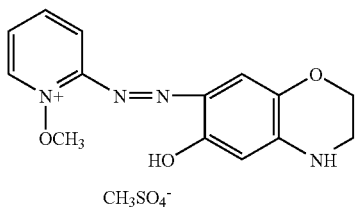

(IV)₇₀
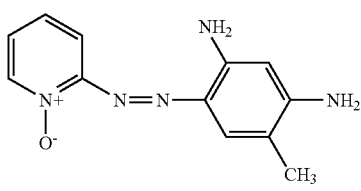

(IV)₇₁
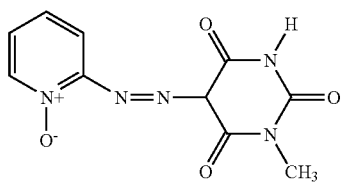

(IV)₇₂
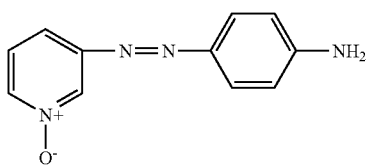

(IV)₇₃
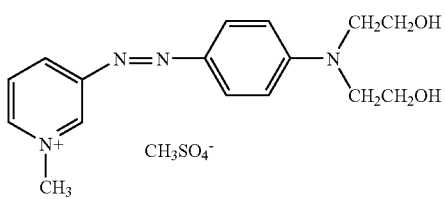

(IV)₇₄
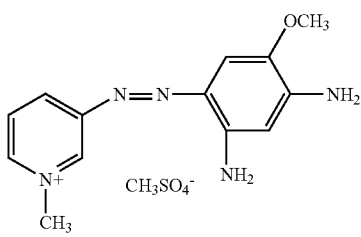

-continued (IV)₇₅
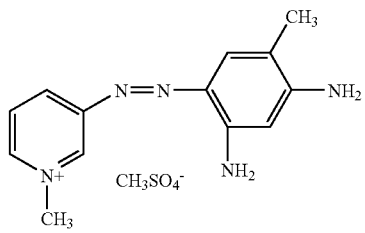

(IV)₇₆
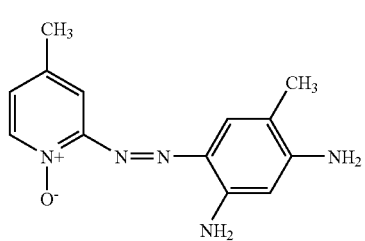

(IV)₇₇
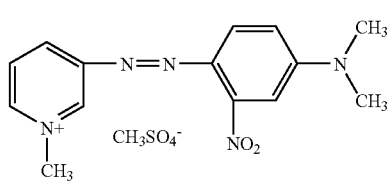

43. A ready-to-use composition for dyeing fibers, comprising:
at least one cationic direct dye chosen from compounds of formulae (I1), (I14), and (IV27) below:

(I1)
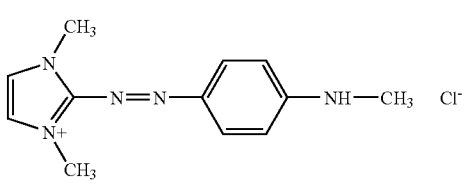

(I14)
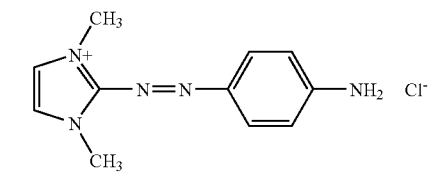

(IV)₂₇
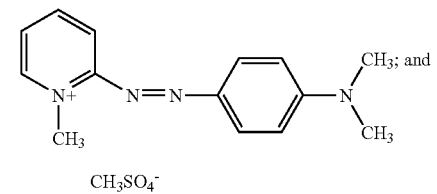

at least one thickening polymer chosen from: diurethane (HMD) of oxyethylated (66 EO) and oxypropylenated (14 PO) $C_{16}$-$C_{18}$ alcohols, crosslinked terpolymers of methacrylic acid/ethlacrylate/steareth 10 allyl ether, and crosspolymers of acrylic acid/$C_{10}$-$C_{30}$ alkyl acrylate.

44. The composition according to claim 31, wherein said at least one oxidation base is present in said composition in an amount sufficient for oxidation dyeing.

45. The composition according to claim 1, wherein said at least one cationic direct dye is present in said composition in an amount sufficient for lightening direct dyeing.

* * * * *

UNITED STATES PATENT AND TRADEMARK OFFICE
CERTIFICATE OF CORRECTION

PATENT NO.       : 7,300,473 B2
APPLICATION NO.  : 11/590853
DATED            : November 27, 2007
INVENTOR(S)      : Gèrard Lang et al.

It is certified that error appears in the above-identified patent and that said Letters Patent is hereby corrected as shown below:

In claim 1, column 42, line 56, before the last structure, insert --and--.

In claim 1, column 43, lines 30-36, " 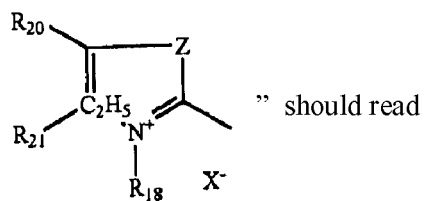 " should read

-- 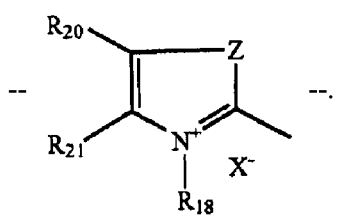 --.

In claim 5, column 51, lines 19-25, " 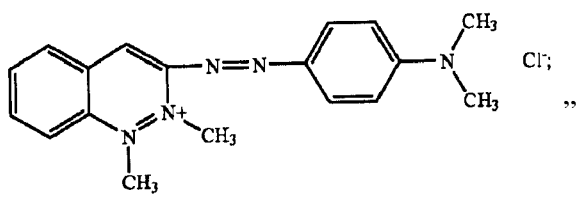 "

should read -- 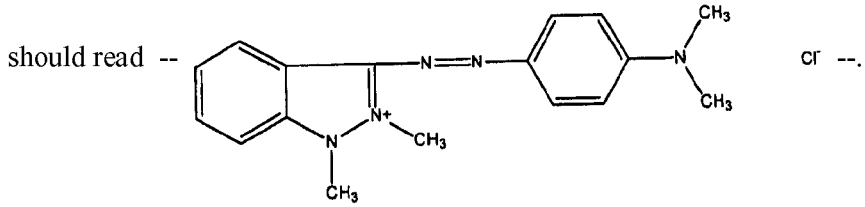 --.

In claim 24, column 52, lines 52-53, "hydroxyethylecellulose," should read --hydroxyethylcellulose,--.

In claim 25, column 52, lines 57-58, "said least" should read --said at least--.

In claim 42, column 60, lines 4-10, " 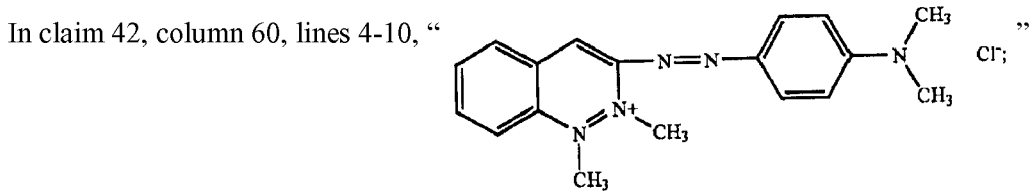 "

should read -- 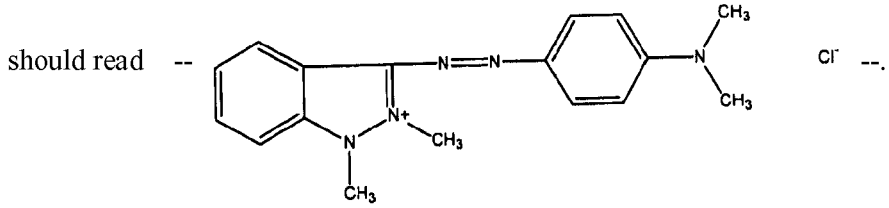 --.

UNITED STATES PATENT AND TRADEMARK OFFICE
CERTIFICATE OF CORRECTION

PATENT NO. : 7,300,473 B2
APPLICATION NO. : 11/590853
DATED : November 27, 2007
INVENTOR(S) : Gèrard Lang et al.

It is certified that error appears in the above-identified patent and that said Letters Patent is hereby corrected as shown below:

In claim 42, column 61, line 23, delete "and".

In claim 42, column 63, lines 9-13

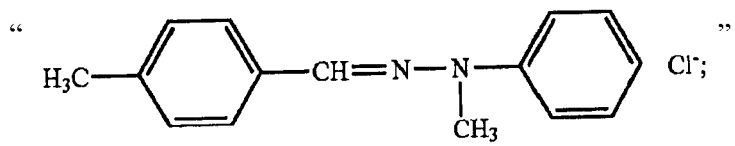

should read

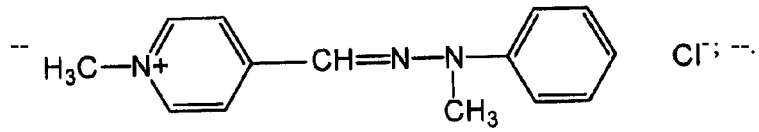

In claim 43, column 75, line 1, "acid/ethlacrylate/steareth" should read --acid/ethacrylate/steareth--.

Signed and Sealed this

Sixth Day of May, 2008

JON W. DUDAS
*Director of the United States Patent and Trademark Office*